(12) United States Patent
Matsumoto

(10) Patent No.: US 11,351,234 B2
(45) Date of Patent: Jun. 7, 2022

(54) DNA VACCINE AGAINST AMYLOID-β AND TAU

(71) Applicant: IMMUNOTHERAPY DEVELOPMENT INC., Saitama (JP)

(72) Inventor: Yoh Matsumoto, Saitama (JP)

(73) Assignee: IMMUNOTHERAPY DEVELOPMENT INC., Saitama (JP)

( * ) Notice: Subject to any disclaimer, the term of this patent is extended or adjusted under 35 U.S.C. 154(b) by 0 days.

(21) Appl. No.: 15/578,123

(22) PCT Filed: Oct. 20, 2016

(86) PCT No.: PCT/JP2016/081038
§ 371 (c)(1),
(2) Date: Nov. 29, 2017

(87) PCT Pub. No.: WO2017/069182
PCT Pub. Date: Apr. 27, 2017

(65) Prior Publication Data
US 2018/0153973 A1 Jun. 7, 2018

(30) Foreign Application Priority Data

Oct. 22, 2015 (JP) .............................. JP2015-207888

(51) Int. Cl.
| | | |
|---|---|---|
| A61K 39/00 | (2006.01) |
| A61K 31/711 | (2006.01) |
| C07K 14/47 | (2006.01) |
| A61K 31/713 | (2006.01) |
| C12N 15/85 | (2006.01) |
| C12N 15/63 | (2006.01) |

(52) U.S. Cl.
CPC ........ *A61K 39/0007* (2013.01); *A61K 31/711* (2013.01); *A61K 31/713* (2013.01); *C07K 14/4711* (2013.01); *C12N 15/63* (2013.01); *C12N 15/85* (2013.01); *A61K 2039/53* (2013.01); *C07K 2319/30* (2013.01)

(58) Field of Classification Search
CPC .............. A61K 39/0007; A61K 31/713; A61K 31/711; A61K 2039/53; C12N 15/63; C07K 14/4711; C07K 2319/30; A61P 25/28

See application file for complete search history.

(56) References Cited

U.S. PATENT DOCUMENTS

| | | | |
|---|---|---|---|
| 2010/0316564 A1* | 12/2010 | Sigurdsson ........ | A61K 39/0005 424/1.49 |
| 2012/0014987 A1 | 1/2012 | Matsumoto | |
| 2013/0122026 A1 | 5/2013 | Matsumoto | |
| 2014/0056901 A1 | 2/2014 | Agadjanyan et al. | |

FOREIGN PATENT DOCUMENTS

| | | | |
|---|---|---|---|
| JP | 2014-103900 A | 6/2014 | |
| JP | 2015-527369 A | 9/2015 | |
| WO | WO 2005/014041 A2 | 2/2005 | |
| WO | WO 2010/110408 A1 | 9/2010 | |
| WO | WO 2014/031697 A2 | 2/2014 | |
| WO | WO-2014031697 A2 * | 2/2014 | ......... A61K 39/0007 |
| WO | WO 2015/017280 A1 | 2/2015 | |

OTHER PUBLICATIONS

Matsumoto et al. Development of a new DNA vaccine for Alzheimer disease targeting a wide range of aβ species and amyloidogenic peptides. PLoS One. Sep. 27, 2013;8(9):e75203. doi: 10.1371/journal.pone.0075203. eCollection 2013.*
Vickers. A vaccine against Alzheimer's disease: developments to date. Drugs Aging 2002; 19(7):487-94.*
Perrin et al. Multimodal techniques for diagnosis and prognosis of Alzheimer's disease. Nature Oct. 15, 2009;461(7266):916-22, Published online Oct. 14, 2009.*
Hampel et al. The future of Alzheimer's disease: the next 10 years. Prog Neurobiol. Dec. 2011;95(4):718-28. Epub Nov. 22, 2011.*
Scior et al. Directed PCR-free engineering of highly repetitive DNA sequences. BMC Biotechnol. Sep. 23, 2011; 11:87. doi: 10.1186/1472-6750-11-87.*
Emily Crow, https://bitesizebio.com/10203/ligation-optimization/, retrieved Feb. 2, 2019.*
Kim et al. Enhancing Th2 immune responses against amyloid protein by a DNA prime-adenovirus boost regimen for Alzheimer's disease. Immunol Lett. Sep. 15, 2007; 112(1): 30-38, published online Jul. 23, 2007.*
Guo et al. A new DNA vaccine fused with the C3d-p28 induces a Th2 immune response against amyloid-beta. Neural Regen Res. Sep. 25, 2013; 8(27): 2581-2590.*
Boche et al., "Reduction of aggregated Tau in neuronal processes but not in the cell bodies after Ab42 immunisation in Alzheimer's disease," Acta Neuropathol, vol. 120, 2010 (published Jun. 9, 2010), pp. 13-20.
International Search Report (Form PCT/ISA/210) for International Application No. PCT/JP2016/081038, dated Jan. 24, 2017.
Okura et al. "Development of Anti-Aβ Vaccination as a Promising Therapy for Alzheimer's Disease," Drug News Perspect, vol. 20, No. 6, Jul./Aug. 2007, pp. 379-386.
Okura et al., "DNA Vaccine Therapy for Alzheimer's Disease: Present Status and Future Direction," Rejuventation Research, vol. 11, No. 2, 2008, pp. 301-308 (9 pages total).

(Continued)

*Primary Examiner* — Gregory S Emch
(74) *Attorney, Agent, or Firm* — Birch, Stewart, Kolasch & Birch, LLP

(57) ABSTRACT

An object of the present invention is to provide a vaccine that can simultaneously reduce Aβ deposition and tau deposition in the brain by means of a single molecule. The present invention provides a recombinant vector comprising DNA encoding amyloid-β, DNA encoding an immunoglobulin Fc sequence, and DNA encoding tau.

11 Claims, 3 Drawing Sheets

Specification includes a Sequence Listing.

(56) References Cited

OTHER PUBLICATIONS

Okura et al., "Nonviral Aβ DNA Vaccine Therapy Against Alzheimer's Disease: Long-Term Effects and Safety," PNAS, vol. 103, No. 25, Jun. 20, 2006, pp. 9619-9624.

Okura et al., "Nonviral DNA Vaccination Augments Microglial Phagocytosis of β-Amyloid Deposits as a Major Clearance Pathway in an Alzheimer's Disease Mouse Model," J Neuropathol Exp Neurol, vol. 67, No. 11, Nov. 2008, pp. 1063-1071.

Okura et al., "Novel Vaccine Therapy for Alzheimer's Disease—Recent Progress and Our Approach," Brain and Nerve, vol. 60, No. 8, Aug. 2008, pp. 931-940, with abstract.

Davtyan et al., "Immunogenicity of DNA- and recombinant protein-based Alzheimer Disease epitope vaccines," Human Vaccines and Immunotherapeutics, vol. 10, Issue 5, May 2014, pp. 1248-1255.

Extended European Search Report for European Application No. 16857495.2, dated Mar. 25, 2019.

Rosenmann et al., "Tauopathy-like Abnormalities and Neurologic Deficits in Mice Immunized With Neutral Tau Protein," Arch Neurol, vol. 63, 2006, pp. 1459-1467.

Rozenstein-Tsalkovich et al., "Repeated Immunization of Mice with Phosphrylated-tau peptides causes neuroinflammation," Experimental Neurology, vol. 248, 2013 (published online Jul. 20, 2013), pp. 451-456.

\* cited by examiner

[Figure 1]
[Figure 2]
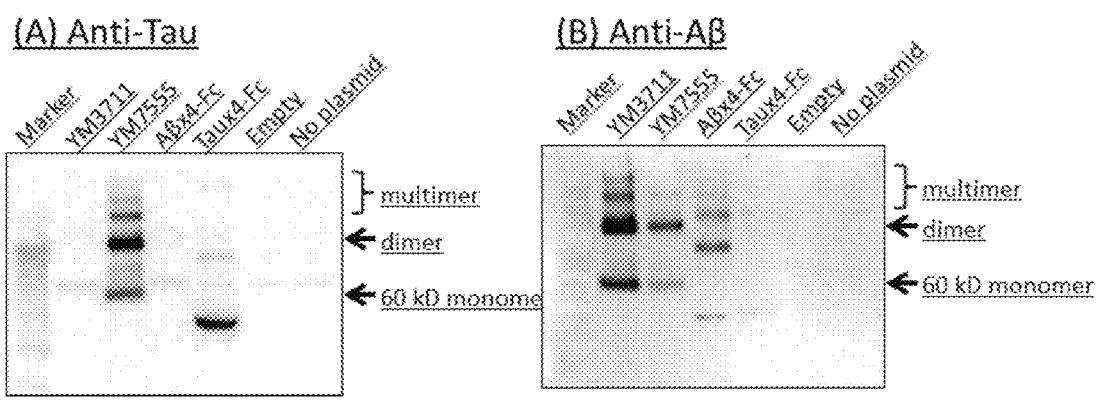
[Figure 3]
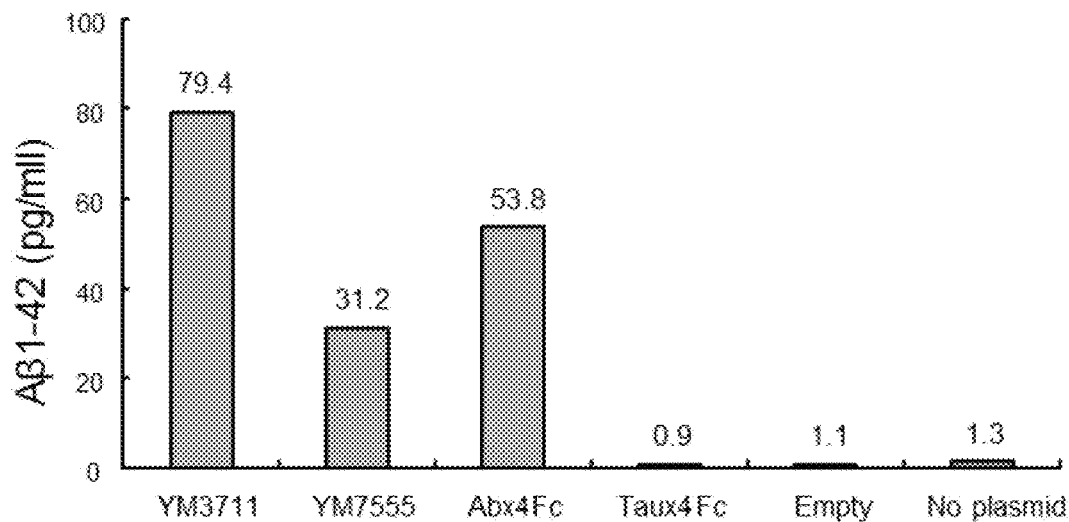

[Figure 4]
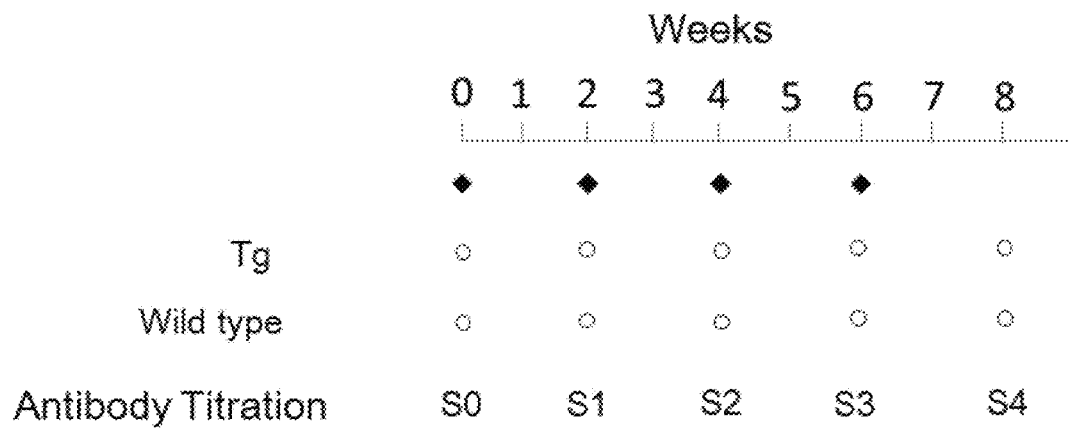
[Figure 5]
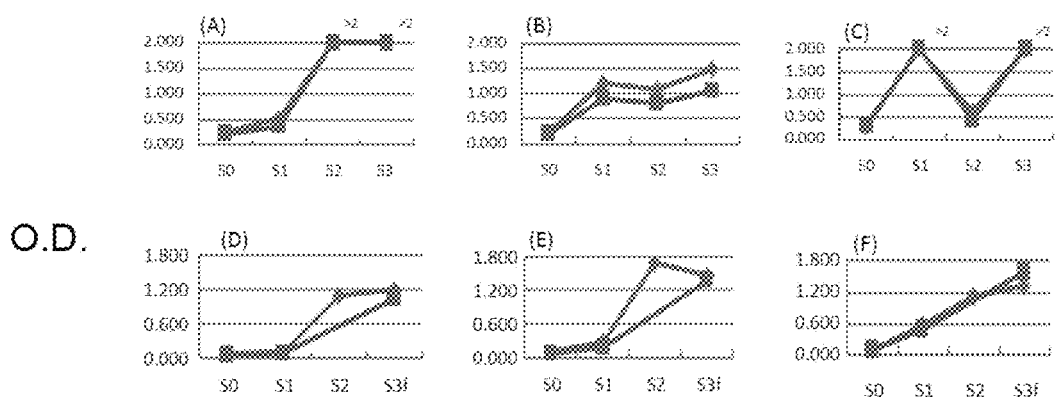
[Figure 6]
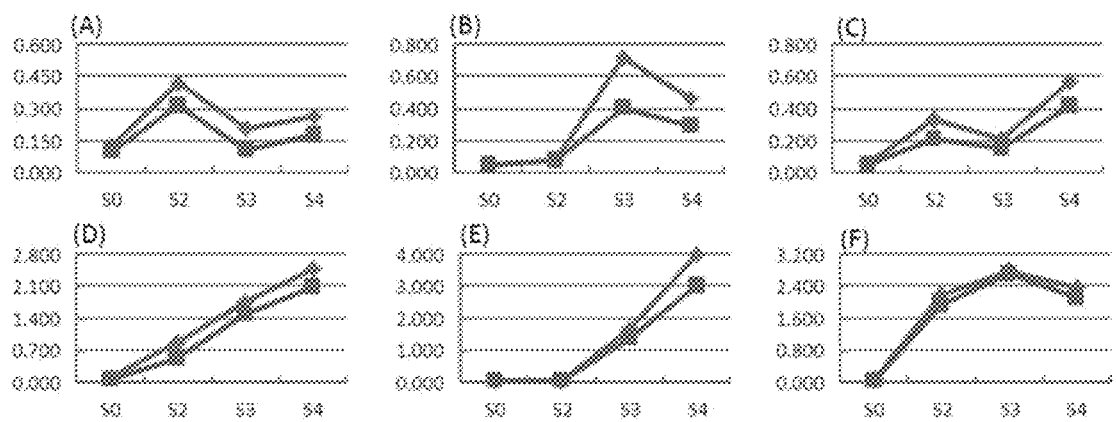

[Figure 7]
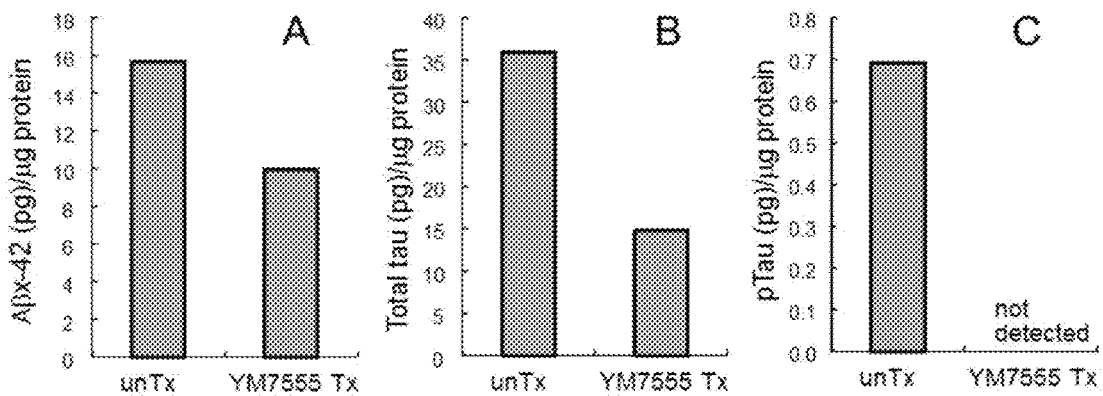
[Figure 8]

DNA VACCINE AGAINST AMYLOID-β AND TAU

TECHNICAL FIELD

The present invention relates to DNA vaccines against amyloid-β and tau.

BACKGROUND ART

Alzheimer's disease is a disease in which moderate to severe cerebral atrophy is grossly visible in the frontal association cortex, temporal lobe, and hippocampal region, and is characterized by three major microscopic findings, i.e., senile plaques (amyloid-β (Aβ) deposition), neurofibrillary tangles (hyperphosphorylated tau deposition), and neuronal loss.

There are many reports that amyloid accumulation precedes tau deposition and neuronal changes, and amyloid accumulation has also been observed in autopsy brains of non-dementia elderly individuals and Down's syndrome individuals. In recent years, the "amyloid hypothesis" has come to be accepted, which assumes that amyloid deposition is positioned uppermost in this pathology, and the prevention of amyloid accumulation would allow subsequent events, such as intraneuronal tau accumulation and neuronal loss, to be prevented to a certain extent.

From pathological examination, however, it has been reported that although anti-immunotherapy effectively reduces Aβ deposition, its effect of reducing tau deposition is extremely weak (Non Patent Literature 1: Boche, D. et al., Acta Neuropathol 120, 13-20).

At present, DNA vaccines against Aβ are known (Patent Literature 1: WO 2010/110408); however, no DNA vaccine is known that can reduce Aβ deposition and tau deposition simultaneously by means of a single molecule.

PRIOR ART DOCUMENTS

Patent Literature

Patent Literature 1: WO 2010/110408

Non Patent Literature

Non Patent Literature 1: Boche, D. et al., Acta Neuropathol 120, 13-20

SUMMARY OF INVENTION

Problems to be Solved by the Invention

The present invention has been made in view of the aforementioned circumstances, and the problem to be solved by the invention is to provide a vaccine that can reduce Aβ deposition and tau deposition in the brain simultaneously by means of a single molecule (single construct).

Means for Solving the Problem

As a result of extensive research to solve the aforementioned problem, the present inventors succeeded in reducing Aβ deposition and tau deposition in the brain simultaneously by means of a single molecule, through the use of a recombinant vector comprising DNA encoding amyloid-β, DNA encoding an immunoglobulin Fc sequence, and DNA encoding tau, thereby completing the present invention.

In summary, the present invention is as set forth below.

(1) A recombinant vector comprising DNA encoding amyloid-β, DNA encoding an immunoglobulin Fc sequence, and DNA encoding tau.

(2) The vector according to (1) above, wherein the DNA encoding amyloid-β is DNA encoding repeats of amyloid-β sequence.

(3) The vector according to (1) or (2) above, wherein the DNA encoding tau is DNA encoding repeats of tau sequence.

(4) The vector according to any of (1) to (3) above, wherein the amyloid-β is Aβ1-42.

(5) A DNA vaccine for prevention or treatment of Alzheimer's disease, comprising the recombinant vector according to any of (1) to (4) above.

(6) A DNA vaccine for reducing brain Aβ and brain tau, comprising the recombinant vector according to any of (1) to (4) above.

(7) An inducer of anti-Aβ antibody and anti-tau antibody, comprising the recombinant vector according to any of (1) to (4) above.

(8) A polypeptide comprising amino acid sequences of amyloid-β, an immunoglobulin Fc sequence, and tau.

(9) The polypeptide according to (8) above, wherein the amyloid-β consists of repeats of amyloid-β sequence.

(10) The polypeptide according to (8) or (9) above, wherein the tau consists of repeats of tau sequence.

(11) The polypeptide according to any of (8) to (10) above, wherein the amyloid-β is Aβ1-42.

(12) A polypeptide expressed from the recombinant vector according to any of (1) to (4) above.

(13) A vaccine for prevention or treatment of Alzheimer's disease, comprising the polypeptide according to any of (8) to (12) above.

(14) A vaccine for reducing brain Aβ and brain tau, comprising the polypeptide according to any of (8) to (12) above.

(15) An inducer of anti-Aβ antibody and anti-tau antibody, comprising the polypeptide according to any of (8) to (12) above.

Advantageous Effects of Invention

According to the present invention, Aβ deposition and tau deposition in the brain can be reduced simultaneously by means of a single molecule.

BRIEF DESCRIPTION OF DRAWINGS

FIG. 1 shows a schematic diagram of the structure of YM7555.

FIG. 2 shows the results of Western blotting detection of protein expression by the recombinant vector of the present invention.

FIG. 3 shows a graph showing the results of ELISA measurement of protein expression by the recombinant vector of the present invention.

FIG. 4 shows the schedule of immunization with YM7555 and blood collection.

FIG. 5 shows the results of induction of anti-Aβ antibody and anti-tau antibody in Tg mice.

FIG. 6 shows the results of induction of anti-Aβ antibody and anti-tau antibody in wild-type mice.

FIG. 7 shows graphs showing the effects of reducing brain Aβ and brain tau according to the present invention.

FIG. 8 shows a schematic diagram of the structure of YM7555P.

DESCRIPTION OF EMBODIMENTS

The present invention will be hereinafter described in detail. The following embodiments are illustrative of the present invention, and are not intended to limit the present invention. The present invention can be carried out in various modes, without departing from the gist of the invention.

1. Summary

At present, a construct comprising DNA encoding Aβ and a DNA vaccine comprising such a construct are known (Patent Literature 1: WO 2010/110408); however, a DNA vaccine that comprises both DNA encoding Aβ and DNA encoding tau, in particular, a DNA vaccine that comprises DNAs encoding repeats of Aβ sequence and repeats of tau sequence, is unknown. One reason for this is that a skilled artisan predicts the possibility that if repeats of Aβ sequence and repeats of tau sequence were combined, the respective sequences would conformationally interfere with each other in the expressed polypeptide, leading to a failure to induce antibodies against Aβ or tau. Even if the skilled artisan attempts to prepare a construct comprising both DNA encoding Aβ and DNA encoding tau, the preparation of such a construct is technically difficult, which is considered to be one reason why such a construct has never been prepared in the past. Specifically, because each of the DNA encoding Aβ and the DNA encoding tau has high hydrophobicity, and the DNA encoding repeats of Aβ sequence and the DNA encoding repeats of tau sequence comprise the repeats, these DNAs are likely to form a conformation due to self-ligation when ligated using a generally known cloning method, and their ligation to a vector or the ligation reaction between the constructs is unlikely to proceed. Thus, it has been technically difficult for the skilled artisan to prepare a construct comprising both the DNA encoding Aβ and the DNA encoding tau, by using a general method.

Even if such a construct can be prepared, it has been extremely difficult to prepare a DNA vaccine that can actually express in vivo a polypeptide comprising Aβ and tau as a single molecule, which polypeptide stimulates the immune system to induce the production of antibodies against Aβ, tau, and their related substances, which antibodies, in turn, can reduce Aβ and tau in the brain simultaneously.

Even if a skilled artisan considers in vivo expression of Aβ and tau, the skilled artisan would generally conceive of combined administration of two types of molecules, i.e., a recombinant vector comprising DNA encoding Aβ and a recombinant vector comprising DNA encoding tau.

In contrast, the present inventors conducted extensive research based on the idea that a DNA vaccine that can reduce Aβ deposition and tau deposition in the brain simultaneously by means of a single molecule would be useful for treatment or prevention of Alzheimer's disease. As a result, the present inventors succeeded in reducing Aβ deposition and tau deposition in the brain simultaneously by means of a single molecule, through the use of a recombinant vector comprising DNA encoding Aβ, DNA encoding an immunoglobulin Fc sequence, and DNA encoding tau, as a DNA vaccine, by employing the unique techniques described in the Examples of the present specification, thereby completing the present invention.

In particular, the recombinant vector of the present invention, by virtue of a synergistic effect of its components, can reduce phosphorylated tau that is strongly neurotoxic in vivo, and thus, is extremely effective for treating or preventing Alzheimer's disease.

The term "simultaneously" as used herein is not necessarily intended to mean simultaneously in time, but also mean both at the same site (cell population).

2. Recombinant Vector and Polypeptide (1) Amyloid-β (Aβ)

Amyloid-β (Aβ) is a polypeptide consisting of 40-43 amino acids cleaved from the precursor protein (APP: amyloid-β protein precursor) by the action of β- and γ-secretases.

The term "Aβ" as used herein refers to a polypeptide comprising 15 or more contiguous amino acids, preferably 20 or more contiguous amino acids, and more preferably refers to a polypeptide having an amino acid sequence consisting of amino acids 1-42 at the N-terminus of Aβ (Aβ1-42), in the native Aβ amino acid sequence.

Nucleotide sequences of DNAs encoding Aβ are available from given databases. For example, the nucleotide sequence as set forth in Genbank accession no. NC_000021.7 can be used as a nucleotide sequence of DNA encoding human Aβ, and the nucleotide sequence as set forth in accession no. NC_000082.5 can be used as a nucleotide sequence of DNA encoding mouse Aβ.

In the present invention, DNAs comprising nucleotide sequences of various regions of Aβ can be prepared by performing PCR using DNA encoding Aβ as a template, and using primers for amplifying desired regions. Examples of such DNAs include DNA encoding a polypeptide having an amino acid sequence consisting of 43 amino acids cleaved by γ-secretase (designated as "Aβ1-43"); DNA encoding a polypeptide having an amino acid sequence consisting of amino acids 1-20 at the N-terminus of Aβ (designated as "Aβ1-20"); DNA encoding a polypeptide having an amino acid sequence consisting of amino acids 1-40 at the N-terminus of Aβ (designated as "Aβ1-40"); and DNA encoding a polypeptide having an amino acid sequence consisting of amino acids 1-42 at the N-terminus of Aβ (designated as "Aβ1-42"). Preferred is the DNA encoding Aβ1-42.

In the present invention, examples of Aβ used in the polypeptide comprising amino acid sequences of amyloid-β (Aβ), an immunoglobulin Fc sequence, and tau (hereinafter also referred to as the "polypeptide of the present invention") include Aβ1-43, Aβ1-20, Aβ1-40, and Aβ1-42, with Aβ1-42 being preferred.

The amino acid sequences of human Aβ1-43, Aβ1-20, Aβ1-40, and Aβ1-42 are shown in SEQ ID NOS: 2, 4, 6, and 8, respectively, and the amino acid sequences of mouse Aβ1-43, Aβ1-20, Aβ1-40, and Aβ1-42 are shown in SEQ ID NOS: 10, 12, 14, and 16, respectively. The nucleotide sequences of DNAs encoding human Aβ1-43, Aβ1-20, Aβ1-40, and Aβ1-42 are shown in SEQ ID NOS: 1, 3, 5, and 7, respectively, and the nucleotide sequences of DNAs encoding mouse Aβ1-43, Aβ1-20, Aβ1-40, and Aβ1-42 are shown in SEQ ID NOS: 9, 11, 13, and 15, respectively.

The DNA encoding human or mouse Aβ1-20, Aβ1-40, or Aβ1-42 can be prepared from the DNA encoding human or mouse Aβ1-43 by using PCR.

In addition to the DNAs encoding human or mouse Aβ1-43, Aβ1-20, Aβ1-40, and Aβ1-42 described above, the following DNAs can be used in the recombinant vector of the present invention:

DNA hybridizing under stringent conditions to DNA consisting of a nucleotide sequence complementary to the nucleotide sequence shown in SEQ ID NO: 1, and encoding a protein having human Aβ activity;

DNA hybridizing under stringent conditions to DNA consisting of a nucleotide sequence complementary to the nucleotide sequence shown in SEQ ID NO: 3, and encoding a protein having human Aβ activity;

DNA hybridizing under stringent conditions to DNA consisting of a nucleotide sequence complementary to the nucleotide sequence shown in SEQ ID NO: 5, and encoding a protein having human Aβ activity;

DNA hybridizing under stringent conditions to DNA consisting of a nucleotide sequence complementary to the nucleotide sequence shown in SEQ ID NO: 7, and encoding a protein having human Aβ activity;

DNA hybridizing under stringent conditions to DNA consisting of a nucleotide sequence complementary to the nucleotide sequence shown in SEQ ID NO: 9, and encoding a protein having mouse Aβ activity;

DNA hybridizing under stringent conditions to DNA consisting of a nucleotide sequence complementary to the nucleotide sequence shown in SEQ ID NO: 11, and encoding a protein having mouse Aβ activity;

DNA hybridizing under stringent conditions to DNA consisting of a nucleotide sequence complementary to the nucleotide sequence shown in SEQ ID NO: 13, and encoding a protein having mouse Aβ activity; and DNA hybridizing under stringent conditions to DNA consisting of a nucleotide sequence complementary to the nucleotide sequence shown in SEQ ID NO: 15, and encoding a protein having mouse Aβ activity.

Each of human Aβ1-43, human Aβ1-20, human Aβ1-40, human Aβ1-42, mouse Aβ1-43, mouse Aβ1-20, mouse Aβ1-40, and mouse Aβ1-42 has its own Aβ activity. Therefore, for example, in the case of a protein expressed from the DNA hybridizing under stringent conditions to DNA consisting of a nucleotide sequence complementary to the nucleotide sequence shown in SEQ ID NO: 1, and encoding a protein having human Aβ activity, it is sufficient for this protein to have Aβ activity equivalent to that of human Aβ1-43. The same also applies to proteins expressed from DNAs hybridizing under stringent conditions to DNAs consisting of nucleotide sequences complementary to the nucleotide sequences shown in other SEQ ID NOS, and encoding proteins having Aβ activity.

The term "stringent conditions" as used herein may refer to any of low-stringency conditions, moderate-stringency conditions, and high-stringency conditions. The "low-stringency conditions" refers to, for example, conditions of 5×SSC, 5×Denhardt's solution, 0.5% SDS, 50% formamide, and 32° C. The "moderate-stringency conditions" refers to, for example, conditions of 5×SSC, 5×Denhardt's solution, 0.5% SDS, 50% formamide, and 42° C. The "high-stringency conditions" refers to, for example, conditions of 5×SSC, 5×Denhardt's solution, 0.5% SDS, 50% formamide, and 50° C. Under these conditions, it is expected that DNA having a higher homology will be efficiently obtained at a higher temperature. A plurality of factors such as temperature, probe concentration, probe length, ionic strength, time, and salt concentration are considered to affect the stringency of hybridization, and a skilled artisan can achieve the same stringency by selecting these factors as appropriate. For detailed hybridization procedures, reference may be made to "Molecular Cloning, A Laboratory Manual (4th edition)" (Cold Spring Harbor Laboratory Press (2012)) and the like.

As the DNA encoding Aβ in the recombinant vector of the present invention, DNA having 50% or more, 60% or more, 70% or more, 80% or more, 90% or more, 95% or more, 98% or more, or 99% or more homology (identity) to the nucleotide sequence shown in SEQ ID NO: 1, 3, 5, or 7, and encoding a protein having human Aβ activity, can be used. Moreover, DNA having 50% or more, 60% or more, 70% or more, 80% or more, 90% or more, 95% or more, 98% or more, or 99% or more homology to the nucleotide sequence shown in SEQ ID NO: 9, 11, 13, or 15, and encoding a protein having mouse Aβ activity, can also be used.

As Aβ in the polypeptide of the present invention, a polypeptide having 70% or more, 80% or more, 85% or more, 90% or more, 95% or more, 98% or more, or 99% or more homology (identity) to the amino acid sequence shown in SEQ ID NO: 2, 4, 6, 8, or 35, and having human Aβ activity, can be used. Preferred as such Aβ is a polypeptide having 85% or more homology to the amino acid sequence shown in SEQ ID NO: 8 or 35 and having human Aβ activity, and more preferred is a polypeptide having 90% or more homology to the amino acid sequence shown in SEQ ID NO: 8 or 35 and having human Aβ activity. Furthermore, as Aβ in the polypeptide of the present invention, a polypeptide having 70% or more, 80% or more, 90% or more, 95% or more, 98% or more, or 99% or more homology to the amino acid sequence shown in SEQ ID NO: 10, 12, 14, or 16, and having mouse Aβ activity, can be used. Preferred as such Aβ is a polypeptide having 85% or more homology to the amino acid sequence shown in SEQ ID NO: 16 and having mouse Aβ activity, and more preferred is a polypeptide having 90% or more homology to the amino acid sequence shown in SEQ ID NO: 16 and having mouse Aβ activity.

In the polypeptide of the present invention, Aβ includes, in addition to the polypeptide consisting of the amino acid sequence shown in SEQ ID NO: 2, 4, 6, 8, or 35, a polypeptide consisting of an amino acid sequence mutated by deletion, substitution, or addition, or a combination thereof, of one or more amino acids in the amino acid sequence shown in SEQ ID NO: 2, 4, 6, 8, or 35, and having human Aβ activity.

Examples of the above-described amino acid sequence mutated by deletion, substitution, or addition, or a combination thereof, of one or more amino acids in the amino acid sequence shown in SEQ ID NO: 2, 4, 6, 8, or 35 include the following:

(i) an amino acid sequence in which 1 to 10 (for example, 1 to 5, preferably 1 to 3, more preferably 1 or 2, and still more preferably 1) amino acids in the amino acid sequence shown in SEQ ID NO: 2, 4, 6, 8, or 35 have been deleted;

(ii) an amino acid sequence in which 1 to 10 (for example, 1 to 5, preferably 1 to 3, more preferably 1 or 2, and still more preferably 1) amino acids in the amino acid sequence shown in SEQ ID NO: 2, 4, 6, 8, or 35 have been substituted with other amino acids;

(iii) an amino acid sequence in which 1 to 10 (for example, 1 to 5, preferably 1 to 3, more preferably 1 or 2, and still more preferably 1) amino acids have been added to the amino acid sequence shown in SEQ ID NO: 2, 4, 6, 8, or 35; and (iv) an amino acid sequence mutated by a combination of (i) to (iii) above.

In the polypeptide of the present invention, Aβ includes, in addition to the polypeptide consisting of the amino acid sequence shown in SEQ ID NO: 10, 12, 14, or 16, a polypeptide consisting of an amino acid sequence mutated by deletion, substitution, or addition, or a combination thereof, of one or more amino acids in the amino acid sequence shown in SEQ ID NO: 10, 12, 14, or 16, and having mouse Aβ activity.

Examples of the above-described amino acid sequence mutated by deletion, substitution, or addition, or a combination thereof, of one or more amino acids in the amino acid sequence shown in SEQ ID NO: 10, 12, 14, or 16 include the following:

(i) an amino acid sequence in which 1 to 10 (for example, 1 to 5, preferably 1 to 3, more preferably 1 or 2, and still more preferably 1) amino acids in the amino acid sequence shown in SEQ ID NO: 10, 12, 14, or 16 have been deleted;

(ii) an amino acid sequence in which 1 to 10 (for example, 1 to 5, preferably 1 to 3, more preferably 1 or 2, and still more preferably 1) amino acids in the amino acid sequence shown in SEQ ID NO: 10, 12, 14, or 16 have been substituted with other amino acids;

(iii) an amino acid sequence in which 1 to 10 (for example, 1 to 5, preferably 1 to 3, more preferably 1 or 2, and still more preferably 1) amino acids have been added to the amino acid sequence shown in SEQ ID NO: 10, 12, 14, or 16; and (iv) an amino acid sequence mutated by a combination of (i) to (iii) above.

The term "Aβ activity" as used herein is intended to mean the activity of Aβ to be produced, accumulate, and/or aggregate in the brain of a subject (such as a human or a mouse) to form Aβ deposition (senile plaques). The Aβ activity can be measured by an immunological technique such as immunohistological staining or ELISA. With immunohistological staining and the like, the Aβ activity can be measured by expressing the protein to be evaluated in the brain of a test animal (such as a mouse), performing immunostaining using anti-Aβ antibody on tissue sections in which the protein has been expressed, and detecting Aβ production, accumulation, aggregation, and/or deposition and the like.

The phrase "having Aβ activity" as used herein is intended to mean having an activity of 10% or more, 20% or more, 30% or more, 40% or more, 50% or more, 60% or more, 70% or more, 80% or more, and preferably 90% or more, compared to the Aβ activity taken as 100% of a polypeptide having the amino acid sequence shown in SEQ ID NO: 2, 4, 6, 8, or 35, or SEQ ID NO: 10, 12, 14, or 16.

For the preparation of polypeptides having the above-described mutations, mutations into polynucleotides can be introduced using a mutagenesis kit that utilizes a site-directed mutagenesis method such as the Kunkel method or Gapped duplex method, for example, QuikChange™ Site-Directed Mutagenesis Kit (Stratagene), GeneTailor™ Site-Directed Mutagenesis System (Invitrogen), or TaKaRa Site-Directed Mutagenesis System (Mutan-K, Mutan-Super Express Km, and the like; Takara Bio). Furthermore, methods such as site-directed mutagenesis methods as described in the following literatures can be used: "Molecular Cloning, A Laboratory Manual (4th edition)" (Cold Spring Harbor Laboratory Press (2012)); "Current Protocols in Molecular Biology" (John Wiley & Sons (1987-1997)); Kunkel (1985) Proc. Natl. Acad. Sci. USA 82: 488-92; Kramer and Fritz (1987) Method. Enzymol. 154: 350-67; Kunkel (1988) Method. Enzymol. 85: 2763-6; and the like.

In the present invention, the DNA encoding Aβ may be DNA encoding repeats of Aβ sequence. A vector comprising the DNA encoding repeats of Aβ sequence can express a plurality of Aβ or a polypeptide comprising the plurality of Aβ. Furthermore, in the polypeptide of the present invention, Aβ may consist of repeats of Aβ sequence. The plurality of Aβ or the polypeptide comprising the plurality of Aβ forms an Aβ oligomer extracellularly. This oligomer stimulates the immune system to induce antibodies against the Aβ oligomer. This is expected to reduce the Aβ oligomer, which is more neurotoxic than the Aβ monomers.

The present invention can exert an enhanced effect of reducing brain Aβ, by comprising repeats of Aβ sequence or DNA encoding the same. The present invention can also induce antibodies against various molecules (such as pEAβ3-42, ABri, and ADan) having neurotoxicity and high amyloid aggregation propensity, by comprising repeats of Aβ sequence or DNA encoding the same.

The range of the number of repeats of Aβ sequence is not limited as long as Aβ forms a folded structure to achieve improved antigenicity over Aβ monomers; the number of repeats of Aβ sequence is preferably 2 to 4, more preferably 3 to 4, and still more preferably 4.

(2) Tau

The recombinant vector of the present invention comprises DNA encoding tau. The polypeptide of the present invention also comprises an amino acid sequence of tau.

Tau is a protein with a molecular weight of about 50,000 that is present in nerve axons or the like, and contributes to microtubular stability.

In the present invention, tau may be either human-derived tau (human tau) or mouse-derived tau (mouse tau), and is preferably human tau. There are six isoforms of tau (0N3R, 1N3R, 0N3R, 2N3R, 1N4R, and 2N4R); however, in the present invention, tau is not limited to any of these isoforms.

Nucleotide sequences of DNAs encoding tau are available from given databases. Examples of the available nucleotide sequence of DNA encoding human tau include, but not limited to, the nucleotide sequence of the DNA encoding isoform 2N4R of tau (Genbank accession no. NM_005910.5). The nucleotide sequence of the DNA encoding human tau (2N4R, full-length) is shown in SEQ ID NO: 17. The amino acid sequence of human tau (2N4R, full-length) is shown in SEQ ID NO: 18.

In the present invention, DNAs comprising nucleotide sequences of various regions of tau can be prepared by performing PCR using DNA encoding tau as a template, and using primers for amplifying desired regions. Examples of such DNAs include DNA encoding a polypeptide (partial polypeptide) comprising/consisting of an amino acid sequence consisting of at least 6 or more, 8 or more, 10 or more, 20 or more, or 30 or more contiguous amino acid residues in the full-length amino acid sequence of tau. Specific examples of the DNA encoding the partial polypeptide include DNA encoding a polypeptide comprising an amino acid sequence consisting of amino acid residues 295 to 305 at the N-terminus of tau (designated as "tau295-305"); and DNA encoding a polypeptide having an amino acid sequence consisting of amino acid residues 379 to 408 at the N-terminus of tau (designated as "tau379-408").

The nucleotide sequences of the DNA encoding human tau295-305 and the DNA encoding human tau379-408 are shown in SEQ ID NOS: 19 and 21, respectively. The amino acid sequences of human tau295-305 and human tau379-408 are shown in SEQ ID NOS: 20 and 22, respectively.

In addition to the DNAs encoding human tau described above, the following DNAs can be used as the DNA encoding tau in the present invention:

DNA hybridizing under stringent conditions to DNA consisting of a nucleotide sequence complementary to the nucleotide sequence shown in SEQ ID NO: 17, and encoding a protein having tau activity;

DNA hybridizing under stringent conditions to DNA consisting of a nucleotide sequence complementary to the nucleotide sequence shown in SEQ ID NO: 19, and encoding a protein having tau activity; and DNA hybridizing under stringent conditions to DNA consisting of a nucleotide sequence complementary to the nucleotide sequence shown in SEQ ID NO: 21, and encoding a protein having tau activity.

Each of human tau, human tau295-305, and human tau379-408 has its own tau activity. Therefore, for example, in the case of a protein expressed from the DNA hybridizing under stringent conditions to DNA consisting of a nucleotide sequence complementary to the nucleotide sequence shown in SEQ ID NO: 17, and encoding a protein having tau activity, it is sufficient for this protein to have tau activity equivalent to that of human tau. The same also applies to proteins expressed from DNAs hybridizing under stringent conditions to DNAs consisting of nucleotide sequences complementary to the nucleotide sequences shown in other SEQ ID NOS, and encoding proteins having tau activity.

The term "stringent conditions" is as defined above.

As the DNA encoding tau in the recombinant vector of the present invention, DNA having 50% or more, 60% or more, 70% or more, 80% or more, 90% or more, 95% or more, 98% or more, or 99% or more homology (identity) to the nucleotide sequence shown in SEQ ID NO: 17, 19, or 21, and encoding a protein having human tau activity, can be used.

As tau in the polypeptide of the present invention, a polypeptide having 70% or more, 80% or more, 85% or more, 90% or more, 95% or more, 98% or more, or 99% or more homology (identity) to the amino acid sequence shown in SEQ ID NO: 18, 20, 22, or 24, and having human tau activity, can be used. Preferred as such tau is a polypeptide having 85% or more homology to the amino acid sequence shown in SEQ ID NO: 18, 20, or 22 and having human tau activity, and more preferred is a polypeptide having 90% or more homology to the amino acid sequence shown in SEQ ID NO: 18, 20, 22, or 24 and having human tau activity.

In the polypeptide of the present invention, tau includes, in addition to the polypeptide consisting of the amino acid sequence shown in SEQ ID NO: 18, 20, 22, or 24, a polypeptide consisting of an amino acid sequence mutated by deletion, substitution, or addition, or a combination thereof, of one or more amino acids in the amino acid sequence shown in SEQ ID NO: 18, 20, 22, or 24, and having human tau activity.

Examples of the above-described amino acid sequence mutated by deletion, substitution, or addition, or a combination thereof, of one or more amino acids in the amino acid sequence shown in SEQ ID NO: 18, 20, 22, or 24 include the following:

(i) an amino acid sequence in which 1 to 10 (for example, 1 to 5, preferably 1 to 3, more preferably 1 or 2, and still more preferably 1) amino acids in the amino acid sequence shown in SEQ ID NO: 18, 20, 22, or 24 have been deleted;

(ii) an amino acid sequence in which 1 to 10 (for example, 1 to 5, preferably 1 to 3, more preferably 1 or 2, and still more preferably 1) amino acids in the amino acid sequence shown in SEQ ID NO: 18, 20, 22, or 24 have been substituted with other amino acids;

(iii) an amino acid sequence in which 1 to 10 (for example, 1 to 5, preferably 1 to 3, more preferably 1 or 2, and still more preferably 1) amino acids have been added to the amino acid sequence shown in SEQ ID NO: 18, 20, 22, or 24; and (iv) an amino acid sequence mutated by a combination of (i) to (iii) above.

The term "tau activity" as used herein is intended to mean the activity of tau to be produced, accumulate, and/or aggregate in the brain of a subject (such as a human or a mouse). The tau activity can be measured by an immunological technique such as immunohistological staining or ELISA. With immunohistological staining, for example, the tau activity can be measured by expressing the protein to be evaluated in the brain of a test animal (such as a mouse), performing immunostaining using anti-tau antibody on tissue sections in which the protein has been expressed, and detecting tau production, accumulation, aggregation, and/or deposition and the like.

The phrase "having human tau activity" as used herein is intended to mean having an activity of 10% or more, 20% or more, 30% or more, 40% or more, 50% or more, 60% or more, 70% or more, 80% or more, and preferably 90% or more, compared to the human tau activity taken as 100% of a polypeptide having the amino acid sequence shown in SEQ ID NO: 18, 20, 22, or 24.

The method for preparing polypeptides having such mutations is as described above.

In the present invention, the DNA encoding tau may be DNA encoding repeats of tau sequence. Furthermore, in the polypeptide of the present invention, tau may consist of repeats of tau sequence. A vector comprising the DNA encoding repeats of tau sequence can express a plurality of tau or a polypeptide comprising the plurality of tau. Examples of the DNA encoding repeats of tau sequence include DNA encoding repeats of human tau295-305 sequence or human tau379-408 sequence. Examples of polypeptides comprising amino acid sequences of repeats of tau sequence include a polypeptide comprising an amino acid sequence of the repeats of human tau295-305 or human tau379-408.

The range of the number of repeats of tau sequence is not limited as long as tau forms a folded structure to achieve improved antigenicity over tau; the number of repeats of tau sequence is preferably 2 to 4, more preferably 3 to 4, and still more preferably 4.

Phosphorylated tau molecules lose their microtubule-binding ability, and are bound together to form aggregates. The recombinant vector and polypeptide of the present invention, by virtue of a synergistic effect of components thereof, can reduce phosphorylated tau that is strongly neurotoxic in vivo, and thus, is extremely effective for treating or preventing Alzheimer's disease.

(3) Immunoglobulin Fc (IgFc) Sequence

The recombinant vector of the present invention comprises DNA encoding an immunoglobulin Fc (IgFc) sequence. The polypeptide of the present invention also comprises an amino acid sequence of the IgFc sequence. Introduction of a gene encoding the IgFc sequence into the living body can promote intracellular transcription and translation of the polypeptides comprising Aβ and tau, and can further promote extracellular release of these polypeptides to more strongly stimulate immune responses against Aβ and tau.

Examples of the IgFc sequence used in the present invention include a human IgFc sequence and a mouse IgFc sequence. The nucleotide sequence as set forth in Genbank accession no. BC014258 can be used as a nucleotide sequence of DNA encoding a human IgFc sequence, and the nucleotide sequence as set forth in accession no. XM_484178.3 can be used as a nucleotide sequence of DNA encoding a mouse IgFc sequence.

SEQ ID NOS of the nucleotide sequences of the DNAs encoding the human and mouse IgFc sequences used in the present invention, as well as the amino acid sequences of these human and mouse IgFc sequences, are shown below:

The nucleotide sequence of the DNA encoding the human IgFc sequence: SEQ ID NO: 25

The amino acid sequence of the human IgFc sequence: SEQ ID NO: 26

The nucleotide sequence of the DNA encoding the mouse IgFc sequence: SEQ ID NO: 27

The amino acid sequence of the mouse IgFc sequence: SEQ ID NO: 28

Each of the nucleotide sequences shown in SEQ ID NOS: 25 and 27 is a nucleotide sequence into which mutations have been introduced to substitute cysteine residues in the original IgFc sequence with serine residues. This is intended to avoid the formation of disulfide bonds.

The following DNAs can also be used as the DNAs encoding the human and mouse IgFc sequences used in the present invention:

DNA hybridizing under stringent conditions to DNA consisting of a nucleotide sequence complementary to the nucleotide sequence shown in SEQ ID NO: 25, and encoding a protein having human IgFc activity; and DNA hybridizing under stringent conditions to DNA consisting of a nucleotide sequence complementary to the nucleotide sequence shown in SEQ ID NO: 27, and encoding a protein having mouse IgFc activity.

The term "IgFc activity" as used herein is intended to mean the activity that promotes intracellular production and extracellular release of the polypeptide comprising the IgFc sequence. For example, the IgFc activity of a certain protein can be measured by expressing a fusion protein of IgFc and a polypeptide of interest in cultured cells, and quantifying an increase in the amount of the polypeptide present in the cultured cells or culture supernatant. The polypeptide can be quantified using an immunological technique such as ELISA or EIA.

As the DNA encoding the IgFc sequence in the recombinant vector of the present invention, DNA having 50% or more, 60% or more, 70% or more, 80% or more, 90% or more, 95% or more, 98% or more, or 99% or more homology to the nucleotide sequence shown in SEQ ID NO: 25, and encoding a protein having human IgFc activity, can be used. Moreover, DNA having 50% or more, 60% or more, 70% or more, 80% or more, 90% or more, 95% or more, 98% or more, or 99% or more homology to the nucleotide sequence shown in SEQ ID NO: 27, and encoding a protein having mouse IgFc activity, can also be used.

The IgFc activity is as described above.

As the IgFc sequence in the polypeptide of the present invention, a polypeptide having 70% or more, 80% or more, 85% or more, 90% or more, 95% or more, 98% or more, or 99% or more homology (identity) to the amino acid sequence shown in SEQ ID NO: 26, and having human IgFc activity, can be used. Preferred as such an IgFc sequence is a polypeptide having 85% or more homology to the amino acid sequence shown in SEQ ID NO: 26 and having human IgFc activity, and more preferred is a polypeptide having 90% or more homology to the amino acid sequence shown in SEQ ID NO: 26 and having human IgFc activity. Furthermore, as the IgFc sequence in the polypeptide of the present invention, a polypeptide having 70% or more, 80% or more, 90% or more, 95% or more, 98% or more, or 99% or more homology to the amino acid sequence shown in SEQ ID NO: 28, and having mouse IgFc activity, can be used. Preferred as such an IgFc sequence is a polypeptide having 85% or more homology to the amino acid sequence shown in SEQ ID NO: 28 and having mouse IgFc activity, and more preferred is a polypeptide having 90% or more homology to the amino acid sequence shown in SEQ ID NO: 28 and having mouse IgFc activity.

In the polypeptide of the present invention, the IgFc sequence includes, in addition to the polypeptide consisting of the amino acid sequence shown in SEQ ID NO: 26, a polypeptide consisting of an amino acid sequence mutated by deletion, substitution, or addition, or a combination thereof, of one or more amino acids in the amino acid sequence shown in SEQ ID NO: 26, and having human IgFc activity.

Examples of the above-described amino acid sequence mutated by deletion, substitution, or addition, or a combination thereof, of one or more amino acids in the amino acid sequence shown in SEQ ID NO: 26 include the following:

(i) an amino acid sequence in which 1 to 10 (for example, 1 to 5, preferably 1 to 3, more preferably 1 or 2, and still more preferably 1) amino acids in the amino acid sequence shown in SEQ ID NO: 26 have been deleted;

(ii) an amino acid sequence in which 1 to 10 (for example, 1 to 5, preferably 1 to 3, more preferably 1 or 2, and still more preferably 1) amino acids in the amino acid sequence shown in SEQ ID NO: 26 have been substituted with other amino acids;

(iii) an amino acid sequence in which 1 to 10 (for example, 1 to 5, preferably 1 to 3, more preferably 1 or 2, and still more preferably 1) amino acids have been added to the amino acid sequence shown in SEQ ID NO: 26; and (iv) an amino acid sequence mutated by a combination of (i) to (iii) above.

In the polypeptide of the present invention, the IgFc sequence includes, in addition to the polypeptide consisting of the amino acid sequence shown in SEQ ID NO: 28, a polypeptide consisting of an amino acid sequence mutated by deletion, substitution, or addition, or a combination thereof, of one or more amino acids in the amino acid sequence shown in SEQ ID NO: 28, and having mouse IgFc activity.

Examples of the above-described amino acid sequence mutated by deletion, substitution, or addition, or a combination thereof, of one or more amino acids in the amino acid sequence shown in SEQ ID NO: 28 include the following:

(i) an amino acid sequence in which 1 to 10 (for example, 1 to 5, preferably 1 to 3, more preferably 1 or 2, and still more preferably 1) amino acids in the amino acid sequence shown in SEQ ID NO: 28 have been deleted;

(ii) an amino acid sequence in which 1 to 10 (for example, 1 to 5, preferably 1 to 3, more preferably 1 or 2, and still more preferably 1) amino acids in the amino acid sequence shown in SEQ ID NO: 28 have been substituted with other amino acids;

(iii) an amino acid sequence in which 1 to 10 (for example, 1 to 5, preferably 1 to 3, more preferably 1 or 2, and still more preferably 1) amino acids have been added to the amino acid sequence shown in SEQ ID NO: 28; and (iv) an amino acid sequence mutated by a combination of (i) to (iii) above.

In another aspect, the recombinant vector of the present invention comprises a polynucleotide comprising DNA encoding amyloid-β, DNA encoding an immunoglobulin Fc sequence, and DNA encoding tau.

Examples of such polynucleotides include, although not limited to, a polynucleotide consisting of the nucleotide sequence shown in SEQ ID NO: 30 (DNA encoding YM7555P). In the recombinant vector of the present invention, in addition to the polynucleotide consisting of the nucleotide sequence shown in SEQ ID NO: 30, the following polynucleotides can be used:

a polynucleotide hybridizing under stringent conditions to a polynucleotide consisting of a nucleotide sequence complementary to the nucleotide sequence shown in SEQ ID NO: 30, and encoding a polypeptide having an activity to induce anti-Aβ antibody and/or anti-tau antibody; and a polynucleotide having 50% or more, 60% or more, 70% or more, 80% or more, 90% or more, 95% or more, 98% or more, or 99% or more (preferably 90% or more) homology (identity) to the nucleotide sequence shown in SEQ ID NO: 30, and encoding a polypeptide having an activity to induce anti-Aβ antibody and/or anti-tau antibody.

The phrase "activity to induce anti-Aβ antibody and/or anti-tau antibody" as used herein is intended to mean an activity to induce anti-Aβ antibody and/or anti-tau antibody in vivo in a mammal serving as a subject (such as a mouse or a human). This activity can be measured by an immunological technique such as immunohistological staining, Western blotting, or ELISA. For example, this activity can be measured by administering the polypeptide of the present invention or the recombinant vector expressing the same to a mammal, collecting blood from the mammal, and measuring the antibody titer of the anti-Aβ antibody and/or the anti-tau antibody in the blood using ELISA.

The phrase "having an activity to induce anti-Aβ antibody and/or anti-tau antibody" is intended to mean having an activity of 10% or more, 20% or more, 30% or more, 40% or more, 50% or more, 60% or more, 70% or more, 80% or more, and preferably 90% or more, compared to the activity taken as 100% of the polypeptide having the amino acid sequence shown in SEQ ID NO: 31.

The term "stringent conditions" is as defined above.

Examples of the polypeptide of the present invention include, although not limited to, a polypeptide consisting of the amino acid sequence shown in SEQ ID NO: 31 (YM7555P). In addition to the polypeptide consisting of the amino acid sequence shown in SEQ ID NO: 31, the following polypeptides can be used as the polypeptide of the present invention:

a polypeptide having 70% or more, 80% or more, 85% or more, 90% or more, 95% or more, 98% or more, or 99% or more (preferably 90% or more) homology (identity) to the amino acid sequence shown in SEQ ID NO: 31, and having an activity to induce anti-Aβ antibody and/or anti-tau antibody; and a polypeptide consisting of an amino acid sequence mutated by deletion, substitution, or addition, or a combination thereof, of one or more amino acids in the amino acid sequence shown in SEQ ID NO: 31, and having an activity to induce anti-Aβ antibody and/or anti-tau antibody.

Examples of the above-described amino acid sequence mutated by deletion, substitution, or addition, or a combination thereof, of one or more amino acids in the amino acid sequence shown in SEQ ID NO: 31 include the following:

(i) an amino acid sequence in which 1 to 10 (for example, 1 to 5, preferably 1 to 3, more preferably 1 or 2, and still more preferably 1) amino acids in the amino acid sequence shown in SEQ ID NO: 31 have been deleted;

(ii) an amino acid sequence in which 1 to 10 (for example, 1 to 5, preferably 1 to 3, more preferably 1 or 2, and still more preferably 1) amino acids in the amino acid sequence shown in SEQ ID NO: 31 have been substituted with other amino acids;

(iii) an amino acid sequence in which 1 to 10 (for example, 1 to 5, preferably 1 to 3, more preferably 1 or 2, and still more preferably 1) amino acids have been added to the amino acid sequence shown in SEQ ID NO: 31; and (iv) an amino acid sequence mutated by a combination of (i) to (iii) above.

(4) Preparation of Recombinant Vector

The recombinant vector of the present invention comprises DNA encoding Aβ, DNA encoding an immunoglobulin Fc (IgFc) sequence, and DNA encoding tau.

The DNA encoding Aβ, tau, or the IgFc sequence may be derived from the same animal species as or different animal species from the animal serving as a subject that will receive the administration of the DNA vaccine; however, it is preferred to use DNA encoding Aβ, tau, or an IgFc sequence derived from the same animal species.

Each of the DNA encoding Aβ, the DNA encoding the IgFc sequence, and the DNA encoding tau has already been cloned. Thus, the DNAs comprised in the vector of the present invention can be obtained using a general genetic engineering technique. For example, a nucleic acid synthesis method using a DNA synthesizer, which is commonly used as a genetic engineering technique, can be used. Moreover, a PCR method that involves isolating or synthesizing DNA sequences for use as templates, designing primers specific for each of the DNAs, and amplifying the gene sequence using a PCR system, or a gene amplification method using a cloning vector, can be used. Furthermore, each of the DNAs can be obtained from a cDNA library or genomic library by performing a known hybridization method such as colony hybridization, plaque hybridization, or Southern blotting, using, as a probe, DNA consisting of the nucleotide sequence shown in SEQ ID NO: 1, 3, 5, 7, 9, 11, 13, 15, 17, 18, 19, 21, 25, or 27, or a fragment thereof. The above-described methods can be readily performed by a skilled artisan in accordance with "Molecular Cloning, A Laboratory Manual (4th edition)" (Cold Spring Harbor Laboratory Press (2012)) and the like. A known method can be used to purify the resulting PCR products.

A general genetic engineering technique can be adopted to prepare the recombinant vector. For example, samples of the DNAs of interest encoding Aβ, tau, and the IgFc sequence are prepared by PCR and the like. PCR can be performed by a general method using KOD polymerase or another DNA polymerase α. The amplified fragments of interest are digested with restriction enzymes, and then inserted into restriction enzyme sites or a multi-cloning site in a plasmid vector such as pCR (registered trademark)-Blunt II-TOPO (registered trademark) vector (Invitrogen). The resulting PCR products are confirmed for their nucleotide sequences with a sequencer to select a plasmid comprising the proper sequence. It is preferred that such a DNA sample can be confirmed as an electrophoretically single plasmid.

As a promoter comprised in the recombinant vector of the present invention, actin promoter, EF1 promoter, CMV promoter, CAG promoter or the like can be used. These promoters may each be ligated to an appropriate plasmid.

The term "stringent conditions" is as defined above. The phrase "having promoter activity" is intended to mean having the transcriptional activity of a gene encoding a structural protein or a non-structural protein.

In the vector of the present invention, the above-described Aβ, tau, and IgFc sequence are comprised in operable form to allow their expression. Specifically, the transgenes (DNAs) are inserted into the vector in a manner that allows expression of the transgenes under the control of appropriate regulatory elements. The DNA encoding Aβ, the DNA encoding the IgFc sequence, and the DNA encoding tau may be individually inserted into different sites in the same vector, or may be inserted contiguously in tandem. The term "regulatory elements" as used herein refers to, for example, promoters, enhancers, and transcription terminators.

The vector of the present invention may carry an additional foreign gene at a position different from the regions into which the DNA encoding Aβ, the DNA encoding the IgFc sequence, and the DNA encoding tau have been inserted. Such a foreign gene may be, for example, although not particularly limited to, a marker gene for vector monitoring, a regulatory gene for the immune system such as a cytokine or hormone, or a signal sequence (leader sequence).

Examples of the recombinant vector of the present invention include the following:

(i) pVAX1 comprising DNA encoding Aβ1-42, DNA encoding the IgFc sequence, and DNA encoding tau, downstream of the CMV promoter;

(ii) pVAX1 comprising DNA encoding repeats of Aβ1-42 sequence, DNA encoding the IgFc sequence, and DNA encoding tau, downstream of the CMV promoter;

(iii) pVAX1 comprising DNA encoding Aβ1-42, DNA encoding the IgFc sequence, and DNA encoding repeats of tau sequence, downstream of the CMV promoter; and (iv) pVAX1 comprising DNA encoding repeats of Aβ1-42 sequence, DNA encoding the IgFc sequence, and DNA encoding repeats of tau sequence, downstream of the CMV promoter.

Examples of "tau" used herein include human tau (full-length), human tau295-305, and human tau379-408, with human tau379-408 being preferred.

Preferably, pVAX1 comprising DNA encoding Aβ1-42, DNA encoding the IgFc sequence, and DNA encoding tau downstream of the CMV promoter comprises an Ig leader (IgL) sequence between the CMV promoter and the DNA encoding Aβ1-42, and comprises a spacer sequence (also referred to as the "linker") between the DNA encoding the IgFc sequence and the DNA encoding tau. More preferably, such pVAX1 comprises the CMV promoter, the Ig leader sequence, the DNA encoding Aβ1-42, the DNA encoding the IgFc sequence, the spacer sequence, and the DNA encoding tau in this order.

Preferably, pVAX comprising DNA encoding repeats of Aβ1-42 sequence, DNA encoding the IgFc sequence, and DNA encoding repeats of tau sequence downstream of the CMV promoter comprises an Ig leader (IgL) sequence between the CMV promoter and the DNA encoding repeats of Aβ1-42 sequence, and comprises spacer sequences between individual "DNAs encoding Aβ1-42" of the DNA encoding repeats of Aβ1-42 sequence, between the DNA encoding the IgFc sequence and the DNA encoding repeats of tau sequence, and between individual "DNAs encoding tau" of the DNA encoding repeats of tau sequence. More preferably, such pVAX1 comprises the CMV promoter, the Ig leader sequence, the DNA encoding repeats of Aβ1-42 sequence, the DNA encoding the IgFc sequence, the spacer sequence, and the DNA encoding repeats of tau sequence in this order (FIG. 1).

The above-described recombinant vectors can comprise DNAs of mouse or human origin. Vectors comprising DNAs of mouse origin can be used in preclinical trials or reagents, while vectors comprising DNAs of human origin can be used in pharmaceutical compositions or reagents.

In accordance with the same technique as described above, a vector that does not comprise the DNA encoding Aβ1-42 but comprises the Ig leader (IgL) sequence, the DNA encoding tau, and the DNA encoding the IgFc sequence can be prepared. Examples of such vectors include a vector comprising IgL-tau×1-huFc (the Ig leader (IgL) sequence, DNA encoding one tau sequence, and DNA encoding the IgFc sequence); and a vector comprising IgL-Tau×4-huFc (the Ig leader (IgL) sequence, DNA encoding four repeats of tau sequence, and DNA encoding the IgFc sequence; also designated herein as "tau×4-IgFc").

(5) Preparation of Polypeptide

The polypeptide of the present invention comprises amino acid sequences of amyloid-β, an immunoglobulin Fc sequence, and tau.

The polypeptide of the present invention can be prepared using a known technique, and can be specifically produced as follows.

(i) Preparation of Expression Vector

The vector for expressing the polypeptide of the present invention is not limited to particular vectors as long as host cells can carry the vector for expression, and examples thereof include plasmid DNAs and bacteriophages. Examples of plasmid DNAs include, although not limited to, plasmid vectors such as pCR (registered trademark)-Blunt II-TOPO (registered trademark) vector (Invitrogen).

As the vector for expressing the polypeptide of the present invention, the recombinant vector prepared in accordance with "(4) Preparation of Recombinant Vector" above can be used. Specifically, the polypeptide of the present invention may be a polypeptide expressed from the recombinant vector comprising DNA encoding amyloid-β, DNA encoding the immunoglobulin Fc sequence, and DNA encoding tau.

(ii) Transformation

Examples of hosts for producing the polypeptide of the present invention include, although not limited to, mammalian cells, bacteria such as *Bifidobacterium bifidum*, lactobacilli, and *E. coli*, insect cells, yeasts, and molds.

The recombinant DNA can be introduced into a host using a known method. Examples of methods for introducing the above-described vector into a host include the calcium phosphate method, the DEAE-dextran method, electroporation, and the cationic lipid method.

The introduction of DNA can be confirmed using selection marker genes (such as ampicillin resistance gene, neomycin resistance gene, hygromycin resistance gene, tetracycline resistance gene, chloramphenicol resistance gene, kanamycin resistant gene, zeocin resistance gene, and blasticidin resistance gene).

(iii) Production of Polypeptide

The polypeptide of the present invention can be obtained by culturing the above-described transformant comprising the polynucleotide encoding the polypeptide or a variant thereof, and collecting the polypeptide from the culture.

The term "culture" refers to any of culture supernatant, cultured cells, cultured bacteria, or cell or bacterial homogenates. The transformant of the present invention is cultured in accordance with a general method used for culturing of a host.

For culturing of a recombinant transfected with an expression vector comprising an inducible transcription promoter as a promoter, an inducer may be added to the medium, as required. When IPTG is used as an inducer, IPTG is added in an amount of 0.1 to 1.0 mM. IPTG is added 2 to 12 hours after the start of culture, and, after the addition, the culture is continued for additional 1 to 12 hours.

If the polypeptide of the present invention accumulates in the bacteria or cells after the culture, the polypeptide of interest is collected by homogenizing the bacteria or cells with a homogenizer and the like. When the polypeptide of the present invention is produced outside the bacteria or cells, the culture is used as is, or the bacteria or cells is removed by, for example, centrifugation. Then, the polypeptide is collected from the culture using ammonium sulfate precipitation procedures and the like, and then isolated and purified, as required, using any of various types of chromatography and the like.

As the cell extract, extracts from eukaryotic or prokaryotic cells can be used, which include, for example, extracts of wheat germ, rabbit reticulocytes, mouse L-cells, HeLa cells, CHO cells, budding yeast, and E. coli. These cell extracts may be concentrated or not concentrated.

(iv) Peptide Synthesis

The polypeptide of the present invention can be obtained by chemical synthesis. Peptide synthesis can be performed by an existing method with a synthesizer. Alternatively, the polypeptide of the present invention can be obtained by requesting the peptide synthesis to and purchasing from a custom peptide synthesis service company.

3. Vaccines (DNA Vaccine Comprising Recombinant Vector and Vaccine Comprising Polypeptide) and Inducer of Anti-Aβ Antibody and Anti-Tau Antibody The present invention provides a DNA vaccine (pharmaceutical composition) for prevention or treatment of Alzheimer's disease, which comprises the above-described recombinant vector. In another aspect, the present invention provides a DNA vaccine for reducing brain Aβ and brain tau, which comprises the above-described vector.

Such a DNA vaccine is intended to induce antibodies against the proteins of interest in a living body by: integrating DNAs encoding the proteins of interest into a vector (a plasmid or virus); administering the vector to the living body; and expressing the proteins of interest in the living body in which the vector has been administered to stimulate the immune system. The DNA vaccine remains in the body for a long time after the administration, and continues to slowly produce the encoded proteins. Thus, excessive immune responses can be avoided. The DNA vaccine can also be modified using a genetic engineering technique.

The present invention also provides a vaccine (pharmaceutical composition) comprising the polypeptide comprising amino acid sequences of amyloid-β, the immunoglobulin Fc sequence, and tau. In another aspect, the present invention provides a vaccine for reducing brain Aβ and brain tau, which comprises the above-described polypeptide.

The term "treatment", "treat", or "treating" as used herein refers to contacting (for example, administering) the vaccine of the present invention with a subject after the onset of a disease, thereby alleviating symptoms of the disease, compared to when the subject is not contacted with the vaccine, and does not completely suppressing the symptoms of the disease. The "onset of a disease" refers to the manifestation of symptoms of the disease in the body.

The term "prevention", "prevent", or "preventing" as used herein refers to contacting (for example, administering) the vaccine of the present invention with a subject before the onset of a disease, thereby alleviating symptoms of the disease after the onset of the disease, compared to when the subject is not contacted with the vaccine, and does not refer to completely suppressing the onset of the disease.

The term "reduction", "reduce", or "reducing" as used herein refers to decreasing the amount of Aβ and/or tau present in the brain, which encompasses decreasing the amount of brain Aβ and/or brain tau accumulated, aggregated, or deposited in the brain. Furthermore, the DNA vaccine of the present invention comprising the above-described vector can also be used as a vaccine for suppressing an increase in the amount of brain Aβ and/or brain tau.

In another aspect, the present invention provides an inducer of anti-Aβ antibody and anti-tau antibody, which comprises the above-described vector or polypeptide.

The presence of various subspecies of neurotoxic Aβ has been recently revealed. Aβ oligomers, which are most intensively analyzed, can be divided into those of low-molecular-weight type formed by aggregation of 2, 3, or 4 molecules, and those of high-molecular-weight type formed by aggregation of 12 or more molecules. Moreover, strong neurotoxicity has also been observed in pEAβ3-42, which is N-terminally truncated and pyrrole-modified by post-translational modification (Saido et al., Neurosci Lett, 215, 173-176, 1996; Schlenzig et al., Biochemistry, 48, 7072-7078, 2009). Furthermore, some findings have been obtained which suggest that molecules such as ABri (Ghiso et al., Brain Pathol, 16, 71-79, 2006) and ADan, which have high amyloid aggregation propensity although completely differing in amino acid sequence from Aβ, are also implicated in the onset of Alzheimer's disease.

The recombinant vector and the polypeptide of the present invention can also induce antibodies against various molecules (such as pEAβ3-42, ABri, and ADan) having neurotoxicity and high amyloid aggregation propensity.

pEAβ3-42 is a molecule produced from Aβ1-42 by N-terminal truncation with glutaminyl cyclase (QC) and post-translational modification (pyrrole modification). pEAβ3-42 is highly neurotoxic, and this molecule itself has a high tendency to aggregate. pEAβ3-42 also acts to enhance the aggregation propensity of unmodified Aβ, and is one of the major factors responsible for lesion formation in Alzheimer's disease.

ABri is a causative molecule for familial British dementia, while ADan is a causative molecule for familial Danish dementia. ABri and ADan are molecules produced by being cleaved as long molecules from their precursor proteins, due to a gene mutation in the stop codon of each precursor protein. ABri and ADan have high amyloid aggregation propensity (amyloid collectively refers to the phenomenon in which small molecules are aggregated and deposited), and are key molecules in the disease progression. ABri and ADan are thus considered to play some role in the lesion formation in Alzheimer's disease.

When the vector of the present invention is used as a DNA vaccine or an inducer of anti-Aβ antibody and anti-tau antibody, gene transfer can be accomplished either by directly administering the vector to a target site of a subject, or by indirectly administering the vector by infecting the vector into the subject-derived cells or other cells for gene transfer, and then injecting the infected cells into a target site. Likewise, when the polypeptide of the present invention is used as a DNA vaccine or an inducer of anti-Aβ antibody and anti-tau antibody, it can be directly administered to a target site of a subject.

Furthermore, the vector or polypeptide of the present invention may be introduced into phospholipid vesicles such as liposomes, for administration of the vesicles. The vesicles carrying the vector or polypeptide of the present invention may be introduced by lipofection into given cells. And then, the resulting cells may be administered systemically, for example, intravenously or intraarterially. The resulting cells may be administered locally to the brain and the like.

Examples of lipids for forming liposome structures include phospholipids, cholesterols, and nitrogen-containing lipids. Phospholipids are generally suitable, which include natural phospholipids such as phosphatidylcholine, phosphatidylserine, phosphatidylglycerol, phosphatidylinositol, phosphatidylethanolamine, phosphatidic acid, cardiolipin, sphingomyelin, egg yolk lecithin, soybean lecithin, and lysolecithin, as well as hydrogenated products thereof obtained in accordance with a standard method. Synthetic phospholipids can also be used, which include dicetyl phosphate, distearoylphosphatidylcholine, dipalmitoylphosphatidylcholine, dipalmitoylphosphatidylethanolamine, dipalmitoylphosphatidylserine, eleostearoylphosphatidylcholine, and eleostearoylphosphatidylethanolamine.

Liposomes can be produced using any method that allows the liposomes to carry the DNA or polypeptide, including, for example, conventional methods such as reverse phase evaporation, ether injection, and surfactant-based techniques.

Lipids including these phospholipids can be used singly or in combinations of two or more. In this case, a lipid containing an atomic group having a cationic group in the molecule, such as ethanolamine or choline, may be used to increase the binding rate of electrically negative DNA. In addition to these major phospholipids for liposome formation, other additives such as cholesterols, stearyl amine, and α-tocopherol, which are generally known as liposome-forming additives, can also be used. The liposomes thus obtained can further contain a membrane fusion promoter, such as polyethylene glycol, in order to enhance their uptake into cells in the affected area or target tissue.

The vaccine, the inducer of anti-Aβ antibody and anti-tau antibody, or the like of the present invention can be formulated in accordance with a routine method, and may comprise pharmaceutically acceptable carriers. Such carriers may be additives, including water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerine, glycerine, propylene glycol, petrolatum, paraffin, stearyl alcohol, stearic acid, human serum albumin, mannitol, sorbitol, lactose, and surfactants acceptable as pharmaceutical additives.

The above-described additives can be selected singly or as an appropriate combination from among those listed above, according to the dosage form of the vaccine or the inducer of anti-Aβ antibody and anti-tau antibody of the present invention. For example, for use as injectable formulations, the purified vector can be dissolved in a solvent (for example, physiological saline, buffer, or glucose solution), and then supplemented with Tween 80, Tween 20, gelatin, human serum albumin, or the like. Alternatively, the vaccine or the inducer may be lyophilized for use as dosage forms that are dissolved before use. Examples of excipients for lyophilization include saccharides such as mannitol, glucose, lactose, sucrose, and sorbitol; starches such as those derived from corn, wheat, rice, potato, and other plants; celluloses such as methylcellulose, hydroxypropylmethylcellulose, and carboxymethylcellulose sodium; gums such as gum arabic and gum tragacanth; gelatin; and collagen.

Examples of subjects to receive the administration of the vaccine, the inducer of anti-Aβ antibody and anti-tau antibody, or the like of the present invention include mammals, including, for example, humans; as well as non-human primates such as monkeys; rodents such as mice and rats; and all other mammals such as rabbits, goats, sheep, pigs, cattle, and dogs; with humans being preferred. Animals (subjects) to receive the administration are, for example, those suffering from Alzheimer's disease, those suspected to have Alzheimer's disease, those showing increased Aβ deposition, those showing increased tau deposition, or those showing neuronal loss. Subjects to receive the administration may also be subjects (patients) in need of treatment and/or prevention of Alzheimer's disease, reduction in brain Aβ and brain tau, and/or induction of anti-Aβ antibody and anti-tau antibody.

The dosage of the vaccine, the inducer of anti-Aβ antibody and anti-tau antibody, or the like of the present invention will vary depending on the age, sex, symptoms, route of administration, frequency of administration, and dosage form. The mode of administration can be selected as appropriate for the age and symptoms of the patient. The effective dosage of the vaccine is an amount of the vaccine required to alleviate the signs or condition of the disease. The therapeutic effect and toxicity of this vaccine can be determined by standard pharmacological procedures in cell culture or in laboratory animals, for example, using ED50 (therapeutically effective dose in 50% of the population) or LD50 (lethal dose for 50% of the population). Likewise, the effective dosage of the inducer of anti-Aβ antibody and anti-tau antibody is an amount of the inducer required to induce detectable levels of anti-Aβ antibody and/or anti-tau antibody in a biological sample (including blood, cells, and tissue) collected from the patient. Anti-Aβ antibody and/or anti-tau antibody can be detected by an immunological technique such as ELISA or immunostaining. A skilled artisan would be able to determine an appropriate dosage for the vaccine or the inducer of anti-Aβ antibody and anti-tau antibody.

The route of administration can be selected as appropriate, and examples of routes of administration include, although not limited to, percutaneous, intranasal, transbronchial, intramuscular, intraperitoneal, intravenous, and subcutaneous routes. Particularly preferred are intramuscular administration and subcutaneous administration. Inoculation may be made at a single site or multiple sites.

The dose ratio between therapeutic and toxic effects is a therapeutic index, and can be expressed as ED50/LD50.

For humans, the vaccine or the inducer of anti-Aβ antibody and anti-tau antibody of the present invention is administered at a single dosage of about 1 to 1000 µg, preferably about 10 to 500 µg, and more preferably about 50 to 250 µg. The frequency of administration may be once or more as long as the side effects are within a clinically acceptable range.

In the previous development of vaccines for Alzheimer's disease, studies have been conducted focusing on antibodies against Aβ and Th2 activity. Thus, it is desirable to measure in advance the antibody titer or cellular immune activity as a vaccine.

For example, the cellular immune activity can be evaluated by separating and culturing lymphocytes from the body, and measuring their $^3$H-thymidine uptake.

Likewise, the Th2 activity can be evaluated by separating plasma from peripheral blood, and measuring its antibody titer by ELISA.

Once the vaccine of the present invention is administered to an animal subject, immune responses against Aβ and/or tau are induced. Specifically, because the above-described amino acid sequence of Aβ1-43, Aβ1-20, Aβ1-40, Aβ1-42, or tau comprises an epitope, antibody production is induced upon administration of the vaccine of the present invention.

Immune responses against Aβ and tau can be detected by measuring the amount of anti-Aβ antibody and anti-tau antibody produced. The amount of the antibodies produced can be measured by a general immunological technique such as ELISA (enzyme-linked immunosorbent assay). Likewise, the therapeutic effect of the vaccine can be confirmed, for example, as a reduction in the amount of Aβ and tau in brain tissues or as a decrease in Aβ deposition (senile plaques). The amount or the state of deposition of Aβ and tau in brain tissues can be observed by immunohistochemistry and the like.

4. Method for Treating and Preventing Alzheimer's Disease, Method for Reducing Brain Aβ and Brain Tau, and Method for Inducing Anti-Aβ Antibody and Anti-Tau Antibody The recombinant vector, polypeptide, and vaccine of the present invention can be used in a method for treating or preventing Alzheimer's disease, a method for reducing brain Aβ and/or brain tau, and a method for inducing anti-Aβ antibody and/or anti-tau antibody. Specifically, the present invention provides a method for treating or preventing Alzheimer's disease, a method for reducing brain Aβ and/or brain tau, and a method for inducing anti-Aβ antibody and/or anti-tau antibody, each comprising administering the recombinant vector or polypeptide of the present invention to a subject.

In the methods of the present invention, the terms "treating", "preventing", and "reducing", as well as the mode of administration, the method of formulation, the dosage form, the target (subject) to receive the administration, the dosage, the route of administration, and the like are as described in the "3." section above.

The present invention will be hereinafter described in detail with reference to Examples; however, the invention is not limited to these Examples.

Example 1

1. Construction of Recombinant Vector (Plasmid) Comprising DNAs Encoding IgL Sequence, Aβ, IgFc Sequence, and Tau (1) Amplification and Cloning of DNAs Encoding IgL Sequence and IgFc Sequence To clone DNAs encoding an immunoglobulin κ leader (hereinafter "IgL") sequence and an immunoglobulin Fc (hereinafter "Fc" or "IgFc") sequence, human peripheral blood-derived mRNA was used as a material to synthesize cDNAs using ReverTra Ace-α-(TOYOBO, Tokyo, Japan). Primers comprising the 5' or 3' end of the nucleotide sequence encoding each sequence and having an appropriate restriction enzyme site (IgL: Bam HI or Xho I; IgFc: Kpn I or Not I) were designed and used to amplify DNAs encoding (or DNAs comprising DNAs encoding) human IgL sequence (SEQ ID NO: 32) and human IgFc sequence using KOD-plus-(Toyobo, Tokyo, Japan). Although the original human IgFc sequence comprises three codons each encoding a cysteine residue near the 5' end, these codons were each modified to encode a serine residue (TGT→TCT or TGC→TCC) during primer design so as to avoid S—S bonding, and the primers thus designed were used to obtain amplification products.

(2) Amplification and Cloning of DNA Encoding Aβ

DNA encoding amyloid-β1-42 (hereinafter "Aβ" or "Aβ1-42") was prepared by oligonucleotide synthesis, provided that two oligonucleotides were first synthesized, which comprised the 5' or 3' end of the nucleotide sequence encoding Aβ and were partially complementary to each other (24 bp in the middle of the Aβ sequence), because a sequence covering the full-length (126 bp) was difficult to synthesize. An appropriate restriction enzyme site (Xho I, Kpn I) was added to each end. After these oligonucleotides were annealed, the entire duplex was prepared by polymerase reaction.

A construct comprising DNA encoding four repeats of Aβ1-42 sequence (hereinafter also referred to as "Aβ×4") (SEQ ID NO: 34) was prepared by ligating four units of Aβ1-42 via three linker sequences (GGTGGCGGTGGCTCG: SEQ ID NO: 29). First, two constructs, i.e., "Aβ1-42+linker sequence+Aβ1-6" and "Aβ37-42+linker sequence+Aβ1-42", were prepared by PCR amplification. Next, both constructs were mixed together and used as a template for PCR amplification with a sense primer designed to have a restriction enzyme site Xho I on the 5'-side of the nucleotide sequence of Aβ1-42 and an antisense primer designed to have a restriction enzyme site Kpn I on the 3'-side of Aβ1-42. The amplification products were electrophoresed on an agarose gel. Among bands that appeared in a ladder pattern, a band of about 560 bp corresponding to the molecular weight of Aβ×4 was excised and purified.

(3) Amplification and Cloning of DNA Encoding Tau

DNA encoding tau379-408 (hereinafter "tau" or "tau379-408") was prepared by preparing a sense strand and an antisense strand by oligonucleotide synthesis, and annealing the strands to form a duplex.

A construct comprising DNA encoding four repeats of tau sequence (hereinafter "tau×4") (SEQ ID NO: 23) was prepared by ligating four units of tau via three linker sequences (GGTGGCGGTGGCTCG: SEQ ID NO: 29). First, two constructs, i.e., "tau379-408+linker sequence+tau1-3" and "tau406-408+linker sequence+tau379-408", were prepared by PCR amplification. Next, both constructs were mixed together and used as a template for PCR amplification with a sense primer designed to have a restriction enzyme site Sal I on the 5'-side of the nucleotide sequence of tau379-408 and an antisense primer designed to have a stop codon and a restriction enzyme site Not I on the 3'-side of tau379-408. The amplification products were electrophoresed on an agarose gel. Among bands that appeared in a ladder pattern, a band of about 420 bp corresponding to the molecular weight of (tau379-408)×4 was excised and purified.

Each of the products obtained in (1), (2), and (3) was inserted into a cloning vector (Zero Blunt TOPO PCR Kit for Sequencing, Invitrogen, Tokyo, Japan), followed by sequence analysis to select a clone having the sequence of interest.

2. Ligation of Four Constructs Comprising DNAs Encoding IgL, Aβ×4, IgFc, and Tau×4

Insertion of DNAs Encoding IgL Sequence, Aβ×4, IgFc Sequence, and tau×4 into Expression Vector DNAs encoding the IgL sequence, (Aβ1-42)×4, and the IgFc sequence were excised from the cloning vectors at the restriction enzyme sites previously added to each DNA, and then purified from an agarose gel (MinElute Gel Extraction Kit, Qiagen, Tokyo, Japan). First, the three constructs of IgL, Aβ×4, and IgFc were ligated together using Ligation High (Toyobo, Tokyo, Japan). To compensate for low ligation efficiency due to the self-ligation of Aβ×4 and the low yield of the ligation product, this ligation product was used as a template for PCR amplification of the IgL-Aβ×4-IgFc ligation sequence, using the same sense primer as that used for the amplification of the IgL sequence (primer comprising the restriction enzyme site BamH I and the 5' end portion of the IgL sequence) and the same antisense primer as that used for the amplification of the IgFc sequence (primer comprising the restriction enzyme site Sal I and the 3' end portion of the IgFc sequence). Without using the TA cloning site, the pTarget vector was cleaved at the two restriction enzyme sites BamH I and Sal I located upstream and downstream, respectively, of the TA cloning site to give the same overhangs as those of the IgL-Aβ×4-IgFc ligation sequence. The IgL-Aβ×4-IgFc ligation sequence and the pTarget vector were electrophoresed on an agarose gel and purified (MinElute Gel Extraction Kit), and then ligated (Ligation High) to give pTarget/IgL-Aβ×4-IgFc. Sequence analysis confirmed that the proper sequence was obtained.

Next, the two restriction enzyme sites Sal I and Not I immediately downstream of the pTarget/IgL-Aβ×4-IgFc insert were cleaved to give the same overhangs as those of the tau×4 construct. Using Ligation High, tau×4 was integrated to complete the IgL-Aβ×4-IgFc-tau×4 ligation sequence within the pTarget vector (pTarget/IgL-Aβ×4-IgFc-tau×4).

3. Insertion of DNA Encoding IgL-Aβ×4-IgFc-tau×4 into Expression Vector

The IgL-Aβ×4-IgFc-tau×4 ligation sequence was cleaved at the restriction enzyme sites BamH I at the 5' end portion and Not I at the 3' end portion, and excised from the pTarget vector. The pVAX1 vector (Life Technologies Japan, Tokyo, Japan) was cleaved at the same BamH I and Not I as those of the insert within the cloning site. The IgL-Aβ×4-IgFc-tau×4 ligation sequence and the pVAX1 vector were each electrophoresed on an agarose gel and then purified, and the resulting products were ligated (Ligation High) to complete a pVAX1/IgL-Aβ×4-IgFc-tau×4 plasmid. The pVAX1/IgL-Aβ×4-IgFc-tau×4 plasmid was produced on a large scale in *E. coli*, and final sequence analysis confirmed that the proper sequence was obtained.

pVAX1/IgL-Aβ×4-IgFc-tau×4 (hereinafter also referred to as "YM7555") was thus obtained as an example recombinant vector comprising DNAs encoding Aβ, the IgFc sequence, and tau. The nucleotide sequence of the obtained pVAX1/IgL-Aβ×4-IgFc-tau×4 insert is shown in SEQ ID NO: 30. The amino acid sequence of the expression product (polypeptide) (YM7555P) of IgL-Aβ×4-IgFc-tau×4 is shown in SEQ ID NO: 31. The amino acid sequences of the IgL sequence, Aβ×4, and tau×4 in YM7555P are shown in SEQ ID NOS: 33, 35, and 24, respectively. FIG. 1 shows a schematic diagram of the structure of IgL-Aβ×4-IgFc-tau×4.

Because the DNA encoding four repeats of Aβ1-42 sequence (denoted as "Aβ×4" or "(Aβ1-42)×4") and the DNA encoding four repeats of tau sequence (denoted as "tau×4" or "(tau379-408)×4") have high hydrophobicity, and comprise the repeats of sequence, these DNAs have a problem that they are likely to form a conformation due to self-ligation when ligated using a generally known cloning method, and their ligation to a vector or the ligation reaction between the constructs is unlikely to proceed.

To solve this problem, in the present Examples, the recombinant vector of the present invention was completed using a combination of the following unique methods developed by the present inventors, i.e., (a) large excess insert method, (b) amplification and ligation method, and (c) 100 colonies method and the like:

(a) Large Excess Insert Method

A general ligation method involves mixing a vector and an insert in a ratio of 1:1 to 1:10; in the present Examples, however, the vector and the insert were mixed in a ratio of 1:10 to 1:1000. For the ligation in the present Examples, an optimum mixing ratio from ratios of 1:10 to 1:1000 was adopted. To prevent self-ligation, the samples were heated at 95° C. for 5 minutes immediately before the ligation.

(b) Amplification and Ligation Method

Appropriate restriction enzyme sites were added to both ends of a construct, and the construct was simultaneously amplified and ligated by PCR with primers having the 5' and 3' terminal nucleotide sequences of the final product.

(c) 100 Colonies Method

Because the above-described insert having repeats is susceptible to self-ligation and mutation, 100 colonies of clones were picked up and stored. Then, plasmids were purified from 12-24 colonies, and sequenced until clones having the plasmid comprising the proper nucleotide sequence were obtained.

4. Recombinant Peptide and the Like

The Aβ1-42 synthetic peptide was purchased from Peptide Institute, Inc. The expression product (YM3711P) of the recombinant vector pVAX1/IgL-(Aβ1-42)×4-huIgFc-huIL-4 (YM3711) (WO 2010/110408) and the expression product (YM7555P) of YM7555 were purified from serum-free culture supernatants of FreeStyle (trademark) 293-F cells (Invitrogen) transfected with YM3711 and YM7555, respectively. Specifically, the culture supernatants were obtained 4 days after the start of culturing the cells transfected with each of YM3711 and YM7555, and filtered. Because YM3711P and YM7555P comprised IgFc, these products were further purified using HiTrap Protein G column (GE Healthcare). Eluates were collected, and confirmed to have strong Aβ immunoreactivity at O.D.280 nm with an anti-Aβ monoclonal antibody, 6E10.

The recombinant tau protein was purchased from Wako Pure Chemical Industries, Ltd.

5. Confirmation of Protein Expression in Cultured Cells

To confirm whether YM7555 induces the protein of interest, the YM7555 plasmid was transfected into HEK293 cells, and the properties of the protein (YM7555P) secreted into the culture supernatants were analyzed by Western blotting with anti-Aβ antibody or anti-tau antibody. YM7555P was also quantitatively analyzed with a commercial sandwich ELISA kit for Aβ quantification.

The results are shown in FIGS. 2 and 3. Western blotting showed that the expression product of YM7555 (YM7555P) was detected with both anti-Aβ antibody and anti-tau antibody, as expected (FIGS. 2A and 2B). Although the estimated molecular weight of the monomer is about 60 kDa, a major band of 120 kDa appeared because the expressed YM7555P tends to form a dimer to multimer. Because the expression product of YM3711 (YM3711P) (monomer: about 60 kDa) and the (Aβ1-42)×4-IgFc product (Aβ×4-Fc) (monomer: about 40 kDa) detected with the anti-Aβ antibody demonstrated similar properties (FIG. 2B), this phenomenon was assumed to be due to the tendency of the repeated structure to form a complex. The expression product of tau×4-IgFc (tau×4-Fc) (monomer: about 40 kDa) was detected only with the anti-tau antibody (FIG. 2A), which confirmed that all the searched products were detected in an antibody-specific manner. Furthermore, a molecule with a molecular weight smaller than about 60 kDa was not detected, which showed that the Aβ1-42 molecule and tau molecule were not separately formed, and an Aβ1-42-tau molecular complex was expressed as a single molecule and released extracellularly.

Since there is no commercial sandwich ELISA kit that recognizes the tau 379-408 sequence, each product was quantified with an ELISA kit for Aβ quantification. As a result, sufficient levels of expression were observed for all the YM3711P, YM7555P, and Aβ×4-Fc products comprising the amino acid sequence of Aβ (FIG. 3). The expression level of YM7555P was relatively lower than that of YM3711P, which was extremely high. This phenomenon was assumed to be due to high hydrophobicity of the translated tau×4 sequence, which causes a burden on the cells, or makes it difficult for the product to be secreted into the culture supernatant as a soluble protein.

In summary, the experiments showed that the polypeptide comprising both Aβ and tau is expressed as a single molecule from the recombinant vector of the present invention.

FIG. 8 shows a schematic diagram of the structure of YM7555P.

6. Induction of Anti-Aβ1-42 Antibody and Anti-Tau Antibody in Tg Mice

New Zealand albino rabbits or 3×Tg mice carrying three-types of familial Alzheimer's disease-related mutated genes (B6; 129-Psen1$^{tm1Mpm}$ Tg(APPSwe,tauP301L)1Lfa/Mmjax) were regularly intramuscularly injected with YM7555, blood was collected with time, and variations in anti-Aβ antibody and anti-tau antibody titers were measured by ELISA. The 3×Tg mice were sacrificed at 2 weeks after the final administration to collect the brains, and the therapeutic effect according to the present invention was evaluated by pathological and immunohistochemical analysis and quantification of proteins in the brain extracts by ELISA.

Initially, the titers of the anti-Aβ antibody and the anti-tau antibody in the 3×Tg mice were measured.

FIG. 4 shows the schedule of immunization with YM7555 and blood collection. Blood was collected from the model mice (Tg) and wild-type mice before the immunization with YM7555 (S0; circles), and the mice were immunized with YM7555 at weeks 0, 2, 4, and 6 (black rhombuses). Blood was collected every 2 weeks after the initial immunization, and antibody titers were measured (white circles; S1, S2, S3, and S4).

The results are shown in FIG. 5. The results of induction of the anti-Aβ antibody in the three Tg mice (changes in titer) are each shown in FIGS. 5A-C, and the results of induction of the anti-tau antibody in the three Tg mice are each shown in FIGS. 5D-F. For both antibodies, the antibody titer began to increase at weeks 4 to 8 after the initial immunization, and showed the maximum value at week 12. The OD value increased about 10-fold compared to the initial value. In FIG. 5, the symbol ♦ indicates the results obtained with 16-fold diluted plasma, and the symbol ■ indicates the results obtained with 32-fold diluted plasma. The temporary decrease in antibody titer for the S2 plasma shown in FIG. 5C is considered to be due to a search error. In FIG. 5, "S0" indicates blood collection before the immunization, and "S1", "S2", "S3", and "S4" indicate blood collection at weeks 2, 4, 6, and 8, respectively. "S3f" indicates that the blood collection at week 6 is the final blood collection.

These results showed that the polypeptide in the form of a single molecule expressed from the recombinant vector of the present invention simultaneously induces the anti-Aβ antibody and the anti-tau antibody at high titers in vivo.

In summary, the recombinant vector of the present invention was shown to be useful as an inducer of the anti-Aβ antibody and the anti-tau antibody.

7. Induction of Anti-Aβ1-42 Antibody and Anti-Tau Antibody in Wild-Type Mice

The similar tests to those in the "6." section above were conducted using wild-type mice instead of the Tg mice.

As a result, the level of increase in the antibody titers of the anti-Aβ antibody and the anti-tau antibody was comparable to that with the Tg mice.

The results are shown in FIG. 6. The results of induction of the anti-Aβ antibody in the three wild-type mice (changes in titer) are each shown in FIGS. 6A-C, and the results of induction of the anti-tau antibody in the three wild-type mice are each shown in FIGS. 6D-F.

8. Reduction in Aβ Deposition and Tau Deposition in Tg Mice

To confirm whether the recombinant vector of the present invention reduces Aβ deposition and tau deposition as intended, 3×Tg mice were regularly administered YM7555, and Aβ and tau in the cerebral cortex (frontal lobe cortex) were quantified by sandwich ELISA. More specifically, the 3×Tg mice were sacrificed at 2 weeks after the final administration of YM7555, the brains were collected, and each of the proteins, i.e., (A) Aβ (Aβ1-42), (B) total tau (Total tau), and (C) phosphorylated tau (pTau), in the brain extracts was quantified by ELISA.

The results are shown in FIG. 7. In FIG. 7, "un Tx" indicates the amount of each protein in Tg mice without the administration of YM7555, and "YM7555 Tx" indicates the amount of each protein in the Tg mice that received the administration of YM7555.

As shown in FIG. 7, the amount of each of the proteins, i.e., (A) Aβ (Aβ1-42), (B) total tau (Total tau), and (C) phosphorylated tau (@Tau), was clearly decreased in the YM7555-treated group. In particular, phosphorylated tau (C) having strong neurotoxicity was not detected at all in the YM7555-treated group, which was an unexpected result.

These results showed that the recombinant vector of the present invention is useful as a DNA vaccine for reducing brain Aβ and brain tau.

The recombinant vector of the present invention was also shown to be extremely useful as a DNA vaccine for the prevention or treatment of Alzheimer's disease, because it reduced brain Aβ and brain tau, which are considered to be causative substances for Alzheimer's disease, and in particular, reduced phosphorylated tau with strong toxicity.

Sequence Listing Free Text

SEQ ID NO: 19: synthetic DNA
SEQ ID NO: 20: synthetic peptide
SEQ ID NO: 21: synthetic DNA
SEQ ID NO: 22: synthetic peptide
SEQ ID NO: 23: synthetic DNA
SEQ ID NO: 24: synthetic peptide
SEQ ID NO: 29: synthetic DNA
SEQ ID NO: 30: synthetic DNA
SEQ ID NO: 31: synthetic peptide
SEQ ID NO: 34: synthetic DNA
SEQ ID NO: 35: synthetic peptide

The invention claimed is:

1. A recombinant vector comprising DNA having a region consisting of (i)-(vi): (i) DNA encoding four (4) repeats of Aβ1-42 or Aβ1-43 sequence, (ii) DNA encoding an immunoglobulin Fc sequence, (iii) DNA encoding four (4) repeats of tau sequence, (iv) optionally DNA encoding an Ig leader sequence, (v) optionally DNA encoding peptide linker/s, and (vi) optionally restriction enzyme sites, wherein the DNA encoding four (4) repeats of tau sequence comprises four (4) repeats of the nucleotide sequences as set forth in SEQ ID NO: 21.

2. The recombinant vector of claim 1, further comprising DNA encoding an Ig leader sequence that is located outside of said region.

3. The recombinant vector of claim 1, wherein the vector does not comprise DNA encoding IL-4.

4. The vector according to claim 1, wherein the amyloid-β is Aβ1-42.

5. The recombinant vector of claim 1, wherein the DNA encoding the repeats of Aβ1-42 or Aβ1-43, the DNA encoding the immunoglobulin Fc sequence, and the DNA encoding the repeats of tau sequence of the region are contained in said order in the region.

6. The vector according to claim 1, wherein the DNA encoding each repeat of Aβ1-42 comprises the nucleotide sequence of SEQ ID NO:7, and wherein the DNA encoding each repeat of tau sequence comprises the nucleotide sequence of SEQ ID NO:21.

7. The recombinant vector of claim 1, wherein the DNA encoding four (4) repeats of tau sequence comprises the nucleotide sequence as set forth in SEQ ID NO: 23.

8. An inducer of anti-Aβ antibody and anti-tau antibody, comprising the recombinant vector according to claim 1.

9. A DNA vaccine for prevention or treatment of Alzheimer's disease, comprising the recombinant vector according to claim 1.

10. A DNA vaccine for reducing brain Aβ and brain tau, comprising the recombinant vector according to claim 1.

11. A polypeptide expressed from the recombinant vector according to claim 1.

* * * * *

SEQUENCE LISTING

```
<160> NUMBER OF SEQ ID NOS: 35

<210> SEQ ID NO 1
<211> LENGTH: 129
<212> TYPE: DNA
<213> ORGANISM: Homo sapiens
<220> FEATURE:
<221> NAME/KEY: CDS
```

<222> LOCATION: (1)..(129)

<400> SEQUENCE: 1

```
gat gca gaa ttc cga cat gac tca gga tat gaa gtt cat cat caa aaa        48
Asp Ala Glu Phe Arg His Asp Ser Gly Tyr Glu Val His His Gln Lys
1               5                   10                  15 ttg gtg ttc ttt gca gaa gat gtg ggt tca aac aaa ggt gca atc att        96
Leu Val Phe Phe Ala Glu Asp Val Gly Ser Asn Lys Gly Ala Ile Ile
                20                  25                  30 gga ctc atg gtg ggc ggt gtt gtc ata gcg aca                           129
Gly Leu Met Val Gly Gly Val Val Ile Ala Thr
                35                  40
```

<210> SEQ ID NO 2
<211> LENGTH: 43
<212> TYPE: PRT
<213> ORGANISM: Homo sapiens

<400> SEQUENCE: 2

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
                35                  40
```

<210> SEQ ID NO 3
<211> LENGTH: 60
<212> TYPE: DNA
<213> ORGANISM: Homo sapiens
<220> FEATURE:
<221> NAME/KEY: CDS
<222> LOCATION: (1)..(60)

<400> SEQUENCE: 3

```
gat gca gaa ttc cga cat gac tca gga tat gaa gtt cat cat caa aaa        48
Asp Ala Glu Phe Arg His Asp Ser Gly Tyr Glu Val His His Gln Lys
1               5                   10                  15 ttg gtg ttc ttt                                                        60
Leu Val Phe Phe
                20
```

<210> SEQ ID NO 4
<211> LENGTH: 20
<212> TYPE: PRT
<213> ORGANISM: Homo sapiens

<400> SEQUENCE: 4

```
Asp Ala Glu Phe Arg His Asp Ser Gly Tyr Glu Val His His Gln Lys
1               5                   10                  15

Leu Val Phe Phe
                20
```

<210> SEQ ID NO 5
<211> LENGTH: 120
<212> TYPE: DNA
<213> ORGANISM: Homo sapiens
<220> FEATURE:
<221> NAME/KEY: CDS
<222> LOCATION: (1)..(120)

<400> SEQUENCE: 5

```
gat gca gaa ttc cga cat gac tca gga tat gaa gtt cat cat caa aaa        48
Asp Ala Glu Phe Arg His Asp Ser Gly Tyr Glu Val His His Gln Lys
```

```
                1               5                   10                  15
ttg gtg ttc ttt gca gaa gat gtg ggt tca aac aaa ggt gca atc att      96
Leu Val Phe Phe Ala Glu Asp Val Gly Ser Asn Lys Gly Ala Ile Ile
                20                  25                  30 gga ctc atg gtg ggc ggt gtt gtc                                      120
Gly Leu Met Val Gly Gly Val Val
        35                  40
```

<210> SEQ ID NO 6
<211> LENGTH: 40
<212> TYPE: PRT
<213> ORGANISM: Homo sapiens

<400> SEQUENCE: 6

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
        35                  40
```

<210> SEQ ID NO 7
<211> LENGTH: 126
<212> TYPE: DNA
<213> ORGANISM: Homo sapiens
<220> FEATURE:
<221> NAME/KEY: CDS
<222> LOCATION: (1)..(126)

<400> SEQUENCE: 7

```
gat gca gaa ttc cga cat gac tca gga tat gaa gtt cat cat caa aaa      48
Asp Ala Glu Phe Arg His Asp Ser Gly Tyr Glu Val His His Gln Lys
1               5                   10                  15 ttg gtg ttc ttt gca gaa gat gtg ggt tca aac aaa ggt gca atc att      96
Leu Val Phe Phe Ala Glu Asp Val Gly Ser Asn Lys Gly Ala Ile Ile
                20                  25                  30 gga ctc atg gtg ggc ggt gtt gtc ata gcg                              126
Gly Leu Met Val Gly Gly Val Val Ile Ala
        35                  40
```

<210> SEQ ID NO 8
<211> LENGTH: 42
<212> TYPE: PRT
<213> ORGANISM: Homo sapiens

<400> SEQUENCE: 8

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
        35                  40
```

<210> SEQ ID NO 9
<211> LENGTH: 129
<212> TYPE: DNA
<213> ORGANISM: Mus musculus
<220> FEATURE:
<221> NAME/KEY: CDS
<222> LOCATION: (1)..(129)

<400> SEQUENCE: 9

```
gat gca gaa ttc gga cat gat tca gga ttt gaa gtc cgc cat caa aaa      48
```

```
Asp Ala Glu Phe Gly His Asp Ser Gly Phe Glu Val Arg His Gln Lys
1               5                   10                  15 ctg gtg ttc ttt gct gaa gat gtg ggt tcg aac aaa ggc gcc atc atc        96
Leu Val Phe Phe Ala Glu Asp Val Gly Ser Asn Lys Gly Ala Ile Ile
            20                  25                  30 gga ctc atg gtg ggc ggc gtt gtc ata gca acc                            129
Gly Leu Met Val Gly Gly Val Val Ile Ala Thr
        35                  40
```

```
<210> SEQ ID NO 10
<211> LENGTH: 43
<212> TYPE: PRT
<213> ORGANISM: Mus musculus

<400> SEQUENCE: 10

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
        35                  40
```

```
<210> SEQ ID NO 11
<211> LENGTH: 60
<212> TYPE: DNA
<213> ORGANISM: Mus musculus
<220> FEATURE:
<221> NAME/KEY: CDS
<222> LOCATION: (1)..(60)

<400> SEQUENCE: 11 gat gca gaa ttc gga cat gat tca gga ttt gaa gtc cgc cat caa aaa       48
Asp Ala Glu Phe Gly His Asp Ser Gly Phe Glu Val Arg His Gln Lys
1               5                   10                  15 ctg gtg ttc ttt                                                        60
Leu Val Phe Phe
            20
```

```
<210> SEQ ID NO 12
<211> LENGTH: 20
<212> TYPE: PRT
<213> ORGANISM: Mus musculus

<400> SEQUENCE: 12

Asp Ala Glu Phe Gly His Asp Ser Gly Phe Glu Val Arg His Gln Lys
1               5                   10                  15

Leu Val Phe Phe
            20
```

```
<210> SEQ ID NO 13
<211> LENGTH: 120
<212> TYPE: DNA
<213> ORGANISM: Mus musculus
<220> FEATURE:
<221> NAME/KEY: CDS
<222> LOCATION: (1)..(120)

<400> SEQUENCE: 13 gat gca gaa ttc gga cat gat tca gga ttt gaa gtc cgc cat caa aaa       48
Asp Ala Glu Phe Gly His Asp Ser Gly Phe Glu Val Arg His Gln Lys
1               5                   10                  15 ctg gtg ttc ttt gct gaa gat gtg ggt tcg aac aaa ggc gcc atc atc       96
Leu Val Phe Phe Ala Glu Asp Val Gly Ser Asn Lys Gly Ala Ile Ile
            20                  25                  30
```

```
gga ctc atg gtg ggc ggc gtt gtc                                        120
Gly Leu Met Val Gly Gly Val Val
        35                  40

<210> SEQ ID NO 14
<211> LENGTH: 40
<212> TYPE: PRT
<213> ORGANISM: Mus musculus

<400> SEQUENCE: 14

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 15
<211> LENGTH: 126
<212> TYPE: DNA
<213> ORGANISM: Mus musculus
<220> FEATURE:
<221> NAME/KEY: CDS
<222> LOCATION: (1)..(126)

<400> SEQUENCE: 15 gat gca gaa ttc gga cat gat tca gga ttt gaa gtc cgc cat caa aaa    48
Asp Ala Glu Phe Gly His Asp Ser Gly Phe Glu Val Arg His Gln Lys
1               5                   10                  15 ctg gtg ttc ttt gct gaa gat gtg ggt tcg aac aaa ggc gcc atc atc    96
Leu Val Phe Phe Ala Glu Asp Val Gly Ser Asn Lys Gly Ala Ile Ile
            20                  25                  30 gga ctc atg gtg ggc ggc gtt gtc ata gca                           126
Gly Leu Met Val Gly Gly Val Val Ile Ala
        35                  40

<210> SEQ ID NO 16
<211> LENGTH: 42
<212> TYPE: PRT
<213> ORGANISM: Mus musculus

<400> SEQUENCE: 16

Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 17
<211> LENGTH: 5811
<212> TYPE: DNA
<213> ORGANISM: Homo sapiens
<220> FEATURE:
<221> NAME/KEY: CDS
<222> LOCATION: (323)..(1648)

<400> SEQUENCE: 17
ggacggccga gcggcagggc gctcgcgcgc gcccactagt ggccggagga gaaggctccc     60
gcggaggccg cgctgcccgc cccctcccct ggggaggctc gcgttcccgc tgctcgcgcc    120
tgcgccgccc gccggcctca ggaacgcgcc ctcttcgccg gcgcgcgccc tcgcagtcac    180
```

```
cgccacccac cagctccggc accaacagca gcgccgctgc caccgcccac cttctgccgc    240
cgccaccaca gccaccttct cctcctccgc tgtcctctcc cgtcctcgcc tctgtcgact    300
atcaggtgaa ctttgaacca gg atg gct gag ccc cgc cag gag ttc gaa gtg    352
                          Met Ala Glu Pro Arg Gln Glu Phe Glu Val
                          1               5                   10
```

| | | | | | | | | | | |
|---|---|---|---|---|---|---|---|---|---|---|
| atg gaa gat cac gct ggg acg tac ggg ttg ggg gac agg aaa gat cag | | | | | | | | | | 400 |
| Met Glu Asp His Ala Gly Thr Tyr Gly Leu Gly Asp Arg Lys Asp Gln | | | | | | | | | | |
|             15                     20                 25 | | | | | | | | | | |

```
ggg ggc tac acc atg cac caa gac caa gag ggt gac acg gac gct ggc    448
Gly Gly Tyr Thr Met His Gln Asp Gln Glu Gly Asp Thr Asp Ala Gly
            30                  35                  40 ctg aaa gaa tct ccc ctg cag acc ccc act gag gac gga tct gag gaa    496
Leu Lys Glu Ser Pro Leu Gln Thr Pro Thr Glu Asp Gly Ser Glu Glu
        45                  50                  55 ccg ggc tct gaa acc tct gat gct aag agc act cca aca gcg gaa gat    544
Pro Gly Ser Glu Thr Ser Asp Ala Lys Ser Thr Pro Thr Ala Glu Asp
60                  65                  70 gtg aca gca ccc tta gtg gat gag gga gct ccc ggc aag cag gct gcc    592
Val Thr Ala Pro Leu Val Asp Glu Gly Ala Pro Gly Lys Gln Ala Ala
75                  80                  85                  90 gcg cag ccc cac acg gag atc cca gaa gga acc aca gct gaa gaa gca    640
Ala Gln Pro His Thr Glu Ile Pro Glu Gly Thr Thr Ala Glu Glu Ala
                95                  100                 105 ggc att gga gac acc ccc agc ctg gaa gac gaa gct gct ggt cac gtg    688
Gly Ile Gly Asp Thr Pro Ser Leu Glu Asp Glu Ala Ala Gly His Val
            110                 115                 120 acc caa gct cgc atg gtc agt aaa agc aaa gac ggg act gga agc gat    736
Thr Gln Ala Arg Met Val Ser Lys Ser Lys Asp Gly Thr Gly Ser Asp
        125                 130                 135 gac aaa aaa gcc aag ggg gct gat ggt aaa acg aag atc gcc aca ccg    784
Asp Lys Lys Ala Lys Gly Ala Asp Gly Lys Thr Lys Ile Ala Thr Pro
140                 145                 150 cgg gga gca gcc cct cca ggc cag aag ggc cag gcc aac gcc acc agg    832
Arg Gly Ala Ala Pro Pro Gly Gln Lys Gly Gln Ala Asn Ala Thr Arg
155                 160                 165                 170 att cca gca aaa acc ccg ccc gct cca aag aca cca ccc agc tct ggt    880
Ile Pro Ala Lys Thr Pro Pro Ala Pro Lys Thr Pro Pro Ser Ser Gly
                175                 180                 185 gaa cct cca aaa tca ggg gat cgc agc ggc tac agc agc ccc ggc tcc    928
Glu Pro Pro Lys Ser Gly Asp Arg Ser Gly Tyr Ser Ser Pro Gly Ser
            190                 195                 200 cca ggc act ccc ggc agc cgc tcc cgc acc ccg tcc ctt cca acc cca    976
Pro Gly Thr Pro Gly Ser Arg Ser Arg Thr Pro Ser Leu Pro Thr Pro
        205                 210                 215 ccc acc cgg gag ccc aag aag gtg gca gtg gtc cgt act cca ccc aag   1024
Pro Thr Arg Glu Pro Lys Lys Val Ala Val Val Arg Thr Pro Pro Lys
220                 225                 230 tcg ccg tct tcc gcc aag agc cgc ctg cag aca gcc ccc gtg ccc atg   1072
Ser Pro Ser Ser Ala Lys Ser Arg Leu Gln Thr Ala Pro Val Pro Met
235                 240                 245                 250 cca gac ctg aag aat gtc aag tcc aag atc ggc tcc act gag aac ctg   1120
Pro Asp Leu Lys Asn Val Lys Ser Lys Ile Gly Ser Thr Glu Asn Leu
                255                 260                 265 aag cac cag ccg gga ggc ggg aag gtg cag ata att aat aag aag ctg   1168
Lys His Gln Pro Gly Gly Gly Lys Val Gln Ile Ile Asn Lys Lys Leu
            270                 275                 280 gat ctt agc aac gtc cag tcc aag tgt ggc tca aag gat aat atc aaa   1216
Asp Leu Ser Asn Val Gln Ser Lys Cys Gly Ser Lys Asp Asn Ile Lys
        285                 290                 295
```

| | | | | | | | | | | | | | | | | |
|---|---|---|---|---|---|---|---|---|---|---|---|---|---|---|---|---|
| cac | gtc | ccg | gga | ggc | ggc | agt | gtg | caa | ata | gtc | tac | aaa | cca | gtt | gac | 1264 |
| His | Val | Pro | Gly | Gly | Gly | Ser | Val | Gln | Ile | Val | Tyr | Lys | Pro | Val | Asp | |
| 300 | | | | | 305 | | | | | 310 | | | | | | |
| ctg | agc | aag | gtg | acc | tcc | aag | tgt | ggc | tca | tta | ggc | aac | atc | cat | cat | 1312 |
| Leu | Ser | Lys | Val | Thr | Ser | Lys | Cys | Gly | Ser | Leu | Gly | Asn | Ile | His | His | |
| 315 | | | | | 320 | | | | | 325 | | | | | 330 | |
| aaa | cca | gga | ggt | ggc | cag | gtg | gaa | gta | aaa | tct | gag | aag | ctt | gac | ttc | 1360 |
| Lys | Pro | Gly | Gly | Gly | Gln | Val | Glu | Val | Lys | Ser | Glu | Lys | Leu | Asp | Phe | |
| | | | 335 | | | | | 340 | | | | | 345 | | | |
| aag | gac | aga | gtc | cag | tcg | aag | att | ggg | tcc | ctg | gac | aat | atc | acc | cac | 1408 |
| Lys | Asp | Arg | Val | Gln | Ser | Lys | Ile | Gly | Ser | Leu | Asp | Asn | Ile | Thr | His | |
| | | 350 | | | | | 355 | | | | | 360 | | | | |
| gtc | cct | ggc | gga | gga | aat | aaa | aag | att | gaa | acc | cac | aag | ctg | acc | ttc | 1456 |
| Val | Pro | Gly | Gly | Gly | Asn | Lys | Lys | Ile | Glu | Thr | His | Lys | Leu | Thr | Phe | |
| | 365 | | | | | 370 | | | | | 375 | | | | | |
| cgc | gag | aac | gcc | aaa | gcc | aag | aca | gac | cac | ggg | gcg | gag | atc | gtg | tac | 1504 |
| Arg | Glu | Asn | Ala | Lys | Ala | Lys | Thr | Asp | His | Gly | Ala | Glu | Ile | Val | Tyr | |
| 380 | | | | | 385 | | | | | 390 | | | | | | |
| aag | tcg | cca | gtg | gtg | tct | ggg | gac | acg | tct | cca | cgg | cat | ctc | agc | aat | 1552 |
| Lys | Ser | Pro | Val | Val | Ser | Gly | Asp | Thr | Ser | Pro | Arg | His | Leu | Ser | Asn | |
| 395 | | | | | 400 | | | | | 405 | | | | | 410 | |
| gtc | tcc | tcc | acc | ggc | agc | atc | gac | atg | gta | gac | tcg | ccc | cag | ctc | gcc | 1600 |
| Val | Ser | Ser | Thr | Gly | Ser | Ile | Asp | Met | Val | Asp | Ser | Pro | Gln | Leu | Ala | |
| | | | | 415 | | | | | 420 | | | | | 425 | | |
| acg | cta | gct | gac | gag | gtg | tct | gcc | tcc | ctg | gcc | aag | cag | ggt | ttg | tga | 1648 |
| Thr | Leu | Ala | Asp | Glu | Val | Ser | Ala | Ser | Leu | Ala | Lys | Gln | Gly | Leu | | |
| | | 430 | | | | | 435 | | | | | 440 | | | | |

| | | | | |
|---|---|---|---|---|
| tcaggcccct | ggggcggtca | ataattgtgg | agaggagaga | atgagagagt gtggaaaaaa | 1708 |
| aaagaataat | gacccggccc | cgccctctg | cccccagctg | ctcctcgcag ttcggttaat | 1768 |
| tggttaatca | cttaacctgc | ttttgtcact | cggctttggc | tcgggacttc aaaatcagtg | 1828 |
| atgggagtaa | gagcaaattt | catctttcca | aattgatggg | tggctagta ataaatatt | 1888 |
| taaaaaaaaa | cattcaaaaa | catggccaca | tccaacattt | cctcaggcaa ttcctttttga | 1948 |
| ttcttttttc | ttcccccctcc | atgtagaaga | gggagaagga | gaggctctga aagctgcttc | 2008 |
| tgggggattt | caagggactg | ggggtgccaa | ccacctctgg | ccctgttgtg ggggtgtcac | 2068 |
| agaggcagtg | gcagcaacaa | aggatttgaa | acttggtgtg | ttcgtggagc cacaggcaga | 2128 |
| cgatgtcaac | cttgtgtgag | tgtgacgggg | gttggggtgg | ggcgggaggc cacggggggag | 2188 |
| gccgaggcag | ggctgggca | gaggggagag | gaagcacaag | aagtgggagt gggagaggaa | 2248 |
| gccacgtgct | ggagagtaga | catccccctc | cttgccgctg | ggagagccaa ggcctatgcc | 2308 |
| acctgcagcg | tctgagcggc | cgcctgtcct | tggtggccgg | gggtgggggc ctgctgtggg | 2368 |
| tcagtgtgcc | accctctgca | gggcagcctg | tgggagaagg | gacagcgggt aaaagagaa | 2428 |
| ggcaagctgg | caggagggtg | gcacttcgtg | gatgacctcc | ttagaaaaga ctgaccttga | 2488 |
| tgtcttgaga | gcgctggcct | cttcctcct | cctgcaggg | tagggggcct gagttgaggg | 2548 |
| gcttccctct | gctccacaga | aaccctgttt | tattgagttc | tgaaggttgg aactgctgcc | 2608 |
| atgattttgg | ccactttgca | gacctgggac | tttagggcta | accagttctc tttgtaagga | 2668 |
| cttgtgcctc | ttgggagacg | tccacccgtt | tccaagcctg | ggccactggc atctctggag | 2728 |
| tgtgtggggg | tctggggagg | aggtcccgag | cccctgtcc | ttcccacggc cactgcagtc | 2788 |
| acccccgtctg | cgccgctgtg | ctgttgtctg | ccgtgagagc | ccaatcactg cctatacccc | 2848 |
| tcatcacacg | tcacaatgtc | ccgaattccc | agcctcacca | ccccttctca gtaatgaccc | 2908 |

```
tggttggttg caggaggtac ctactccata ctgagggtga aattaaggga aggcaaagtc   2968
caggcacaag agtgggaccc cagcctctca ctctcagttc cactcatcca actgggaccc   3028
tcaccacgaa tctcatgatc tgattcggtt ccctgtctcc tcctcccgtc acagatgtga   3088
gccagggcac tgctcagctg tgaccctagg tgtttctgcc ttgttgacat ggagagagcc   3148
cttccccctg agaaggcctg gccccttcct gtgctgagcc cacagcagca ggctgggtgt   3208
cttggttgtc agtggtggca ccaggatgga agggcaaggc acccagggca ggcccacagt   3268
cccgctgtcc cccacttgca ccctagcttg tagctgccaa cctcccagac agcccagccc   3328
gctgctcagc tccacatgca tagtatcagc cctccacacc cgacaaaggg gaacacaccc   3388
ccttggaaat ggttcttttc ccccagtccc agctggaagc catgctgtct gttctgctgg   3448
agcagctgaa catatacata gatgttgccc tgccctcccc atctgcaccc tgttgagttg   3508
tagttggatt tgtctgttta tgcttggatt caccagagtg actatgatag tgaaaagaaa   3568
aaaaaaaaaa aaaaggacg catgtatctt gaaatgcttg taaagaggtt tctaacccac   3628
cctcacgagg tgtctctcac ccccacactg ggactcgtgt ggcctgtgtg gtgccaccct   3688 gctgggcct cccaagttt gaaaggcttt cctcagcacc tgggacccaa cagagaccag   3748
cttctagcag ctaaggaggc cgttcagctg tgacgaaggc ctgaagcaca ggattaggac   3808
tgaagcgatg atgtcccctt ccctacttcc ccttggggct ccctgtgtca gggcacagac   3868
taggtcttgt ggctggtctg gcttgcgcg cgaggatggt tctctctggt catagcccga   3928
agtctcatgg cagtcccaaa ggaggcttac aactcctgca tcacaagaaa aaggaagcca   3988
ctgccagctg gggggatctg cagctcccag aagctccgtg agcctcagcc acccctcaga   4048
ctgggttcct ctccaagctc gccctctgga ggggcagcgc agcctcccac caagggccct   4108
gcgaccacag cagggattgg gatgaattgc ctgtcctgga tctgctctag aggcccaagc   4168
tgcctgcctg aggaaggatg acttgacaag tcaggagaca ctgttcccaa agccttgacc   4228
agagcacctc agcccgctga ccttgcacaa actccatctg ctgccatgag aaaagggaag   4288
ccgcctttgc aaaacattgc tgcctaaaga aactcagcag cctcaggccc aattctgcca   4348
cttctggttt gggtacagtt aaaggcaacc ctgagggact tggcagtaga aatccagggc   4408
ctcccctggg gctggcagct tcgtgtgcag ctagagcttt acctgaaagg aagtctctgg   4468
gcccagaact ctccaccaag agcctccctg ccgttgctg agtcccagca attctcctaa   4528
gttgaaggga tctgagaagg agaaggaaat gtggggtaga tttggtggtg gttagagata   4588
tgcccccctc attactgcca acagtttcgg ctgcatttct tcacgcacct cggttcctct   4648
tcctgaagtt cttgtgccct gctcttcagc accatgggcc ttcttatacg gaaggctctg   4708
ggatctcccc cttgtggggc aggctcttgg ggccagccta agatcatggt ttagggtgat   4768
cagtgctggc agataaattg aaaaggcacg ctggcttgtg atcttaaatg aggacaatcc   4828
ccccagggct gggcactcct cccctcccct cacttctccc acctgcagag ccagtgtcct   4888
tgggtgggct agataggata tactgtatgc cggctccttc aagctgctga ctcactttat   4948
caatagttcc atttaaattg acttcagtgg tgagactgta tcctgtttgc tattgcttgt   5008
tgtgctatgg ggggagggg gaggaatgtg taagatagtt aacatgggca aagggagatc   5068
ttggggtgca gcacttaaac tgcctcgtaa cccttttcat gatttcaacc acatttgcta   5128
gagggaggga gcagccacgg agttagaggc ccttgggtt tctcttttcc actgacaggc   5188
tttcccaggc agctggctag ttcattccct ccccagccag gtgcaggcgt aggaatatgg   5248
acatctggtt gctttggcct gctgccctct ttcagggtc ctaagcccac aatcatgcct   5308
```

```
ccctaagacc ttggcatcct tccctctaag ccgttggcac ctctgtgcca cctctcacac    5368
tggctccaga cacacagcct gtgcttttgg agctgagatc actcgcttca ccctcctcat    5428
ctttgttctc caagtaaagc cacgaggtcg gggcgagggc agaggtgatc acctgcgtgt    5488
cccatctaca gacctgcagc ttcataaaac ttctgatttc tcttcagctt tgaaaagggt    5548
taccctgggc actggcctag agcctcacct cctaatagac ttagccccat gagtttgcca    5608
tgttgagcag gactatttct ggcacttgca agtcccatga tttcttcggt aattctgagg    5668 gtgggggag ggacatgaaa tcatcttagc ttagctttct gtctgtgaat gtctatatag     5728
tgtattgtgt gttttaacaa atgatttaca ctgactgttg ctgtaaaagt gaatttggaa    5788
ataaagttat tactctgatt aaa                                           5811
```

<210> SEQ ID NO 18
<211> LENGTH: 441
<212> TYPE: PRT
<213> ORGANISM: Homo sapiens

<400> SEQUENCE: 18

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
```

```
                    275                 280                 285
Ser Lys Cys Gly Ser Lys Asp Asn Ile Lys His Val Pro Gly Gly Gly
                290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
                355                 360                 365

Lys Lys Ile Glu Thr His Lys Leu Thr Phe Arg Glu Asn Ala Lys Ala
                370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
                435                 440

<210> SEQ ID NO 19
<211> LENGTH: 33
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(33)

<400> SEQUENCE: 19 gat aat atc aaa cac gtc ccg gga ggc ggc agt                         33
Asp Asn Ile Lys His Val Pro Gly Gly Gly Ser
1               5                  10

<210> SEQ ID NO 20
<211> LENGTH: 11
<212> TYPE: PRT
<213> ORGANISM: Artificial
<220> FEATURE:
<223> OTHER INFORMATION: Synthetic Construct

<400> SEQUENCE: 20

Asp Asn Ile Lys His Val Pro Gly Gly Gly Ser
1               5                  10

<210> SEQ ID NO 21
<211> LENGTH: 90
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(90)

<400> SEQUENCE: 21 cgc gag aac gcc aaa gcc aag aca gac cac ggg gcg gag atc gtg tac    48
Arg Glu Asn Ala Lys Ala Lys Thr Asp His Gly Ala Glu Ile Val Tyr
1               5                  10                  15
```

```
aag tcg cca gtg gtg tct ggg gac acg tct cca cgg cat ctc            90
Lys Ser Pro Val Val Ser Gly Asp Thr Ser Pro Arg His Leu
         20                  25                  30
```

<210> SEQ ID NO 22
<211> LENGTH: 30
<212> TYPE: PRT
<213> ORGANISM: Artificial
<220> FEATURE:
<223> OTHER INFORMATION: Synthetic Construct

<400> SEQUENCE: 22

```
Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
         20                  25                  30
```

<210> SEQ ID NO 23
<211> LENGTH: 408
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(408)

<400> SEQUENCE: 23

```
cgc gag aac gcc aaa gcc aag aca gac cac ggg gcg gag atc gtg tac            48
Arg Glu Asn Ala Lys Ala Lys Thr Asp His Gly Ala Glu Ile Val Tyr
1               5                   10                  15 aag tcg cca gtg gtg tct ggg gac acg tct cca cgg cat ctc ggt ggc            96
Lys Ser Pro Val Val Ser Gly Asp Thr Ser Pro Arg His Leu Gly Gly
         20                  25                  30 ggt ggc tcg cgc gag aac gcc aaa gcc aag aca gac cac ggg gcg gag           144
Gly Gly Ser Arg Glu Asn Ala Lys Ala Lys Thr Asp His Gly Ala Glu
     35                  40                  45 atc gtg tac aag tcg cca gtg gtg tct ggg gac acg tct cca cgg cat           192
Ile Val Tyr Lys Ser Pro Val Val Ser Gly Asp Thr Ser Pro Arg His
 50                  55                  60 ctc ggt ggc ggt ggc tcg cgc gag aac gcc aaa gcc aag aca gac cac           240
Leu Gly Gly Gly Gly Ser Arg Glu Asn Ala Lys Ala Lys Thr Asp His
65                  70                  75                  80 ggg gcg gag atc gtg tac aag tcg cca gtg gtg tct ggg gac acg tct           288
Gly Ala Glu Ile Val Tyr Lys Ser Pro Val Val Ser Gly Asp Thr Ser
                 85                  90                  95 cca cgg cat ctc ggt ggc ggt ggc tcg cgc gag aac gcc aaa gcc aag           336
Pro Arg His Leu Gly Gly Gly Gly Ser Arg Glu Asn Ala Lys Ala Lys
            100                 105                 110 aca gac cac ggg gcg gag atc gtg tac aag tcg cca gtg gtg tct ggg           384
Thr Asp His Gly Ala Glu Ile Val Tyr Lys Ser Pro Val Val Ser Gly
        115                 120                 125 gac acg tct cca cgg cat ctc tga                                           408
Asp Thr Ser Pro Arg His Leu
    130                 135
```

<210> SEQ ID NO 24
<211> LENGTH: 135
<212> TYPE: PRT
<213> ORGANISM: Artificial
<220> FEATURE:
<223> OTHER INFORMATION: Synthetic Construct

<400> SEQUENCE: 24

```
Arg Glu Asn Ala Lys Ala Lys Thr Asp His Gly Ala Glu Ile Val Tyr
 1               5                  10                 15

Lys Ser Pro Val Val Ser Gly Asp Thr Ser Pro Arg His Leu Gly Gly
             20                  25                  30

Gly Gly Ser Arg Glu Asn Ala Lys Ala Lys Thr Asp His Gly Ala Glu
         35                  40                  45

Ile Val Tyr Lys Ser Pro Val Val Ser Gly Asp Thr Ser Pro Arg His
 50                  55                  60

Leu Gly Gly Gly Ser Arg Glu Asn Ala Lys Ala Lys Thr Asp His
 65                  70                  75                  80

Gly Ala Glu Ile Val Tyr Lys Ser Pro Val Val Ser Gly Asp Thr Ser
                 85                  90                  95

Pro Arg His Leu Gly Gly Gly Ser Arg Glu Asn Ala Lys Ala Lys
             100                 105                 110

Thr Asp His Gly Ala Glu Ile Val Tyr Lys Ser Pro Val Val Ser Gly
             115                 120                 125

Asp Thr Ser Pro Arg His Leu
         130                 135

<210> SEQ ID NO 25
<211> LENGTH: 696
<212> TYPE: DNA
<213> ORGANISM: Homo sapiens
<220> FEATURE:
<221> NAME/KEY: CDS
<222> LOCATION: (1)..(696)

<400> SEQUENCE: 25 gag ccc aaa tct tct gac aaa act cac aca tcc cca ccg tcc cca gca      48
Glu Pro Lys Ser Ser Asp Lys Thr His Thr Ser Pro Pro Ser Pro Ala
 1               5                  10                  15 cct gaa ctc ctg ggg gga ccg tca gtc ttc ctc ttc ccc cca aaa ccc      96
Pro Glu Leu Leu Gly Gly Pro Ser Val Phe Leu Phe Pro Pro Lys Pro
             20                  25                  30 aag gac acc ctc atg atc tcc cgg acc cct gag gtc aca tgc gtg gtg     144
Lys Asp Thr Leu Met Ile Ser Arg Thr Pro Glu Val Thr Cys Val Val
         35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
 50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
 65                  70                  75                  80 tac aac agc acg tac cgt gtg gtc agc gtc ctc acc gtc ctg cac cag     288
Tyr Asn Ser Thr Tyr Arg Val Val Ser Val Leu Thr Val Leu His Gln
                 85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
             100                 105                 110 ctc cca gcc ccc atc gag aaa acc atc tcc aaa gcc aaa ggg cag ccc     384
Leu Pro Ala Pro Ile Glu Lys Thr Ile Ser Lys Ala Lys Gly Gln Pro
         115                 120                 125 cga gaa cca cag gtg tac acc ctg ccc cca tcc cgg gat gag ctg acc     432
Arg Glu Pro Gln Val Tyr Thr Leu Pro Pro Ser Arg Asp Glu Leu Thr
     130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
```

```
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac      576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc      624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag      672
Ser Cys Ser Val Met His Glu Ala Leu His Asn His Tyr Thr Gln Lys
    210                 215                 220 agc ctc tcc ctg tct ccg ggt aaa                                      696
Ser Leu Ser Leu Ser Pro Gly Lys
225                 230

<210> SEQ ID NO 26
<211> LENGTH: 232
<212> TYPE: PRT
<213> ORGANISM: Homo sapiens

<400> SEQUENCE: 26

Glu Pro Lys Ser Ser Asp Lys Thr His Thr Ser Pro Pro Ser Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 27
<211> LENGTH: 711
<212> TYPE: DNA
<213> ORGANISM: Mus musculus
<220> FEATURE:
<221> NAME/KEY: CDS
```

```
<222> LOCATION: (1)..(711)

<400> SEQUENCE: 27 gag ccc cgg gtg ccc atc acc cag aac ccc agc ccc cca ctg aaa gag      48
Glu Pro Arg Val Pro Ile Thr Gln Asn Pro Ser Pro Pro Leu Lys Glu
1               5                   10                  15 agc ccc ccc tct gcc gct cct gat ctg ctg ggc gga ccc agc gtg ttc      96
Ser Pro Pro Ser Ala Ala Pro Asp Leu Leu Gly Gly Pro Ser Val Phe
            20                  25                  30 atc ttc cca ccc aag atc aag gac gtg ctg atg atc agc ctg agc ccc     144
Ile Phe Pro Pro Lys Ile Lys Asp Val Leu Met Ile Ser Leu Ser Pro
        35                  40                  45 atg gtg acc agc gtg gtg gtg gac gtg tcc gag gac gac ccc gac gtg     192
Met Val Thr Ser Val Val Val Asp Val Ser Glu Asp Asp Pro Asp Val
    50                  55                  60 cag atc agt tgg ttc gtg aac aac gtg gag gtg cac acc gcc cag acc     240
Gln Ile Ser Trp Phe Val Asn Asn Val Glu Val His Thr Ala Gln Thr
65                  70                  75                  80 cag acc cac cgg gag gac tac aac agc acc ctg aga gtg gtg tcc gcc     288
Gln Thr His Arg Glu Asp Tyr Asn Ser Thr Leu Arg Val Val Ser Ala
                85                  90                  95 ctg ccc atc cag cac cag gac tgg atg agc ggc aaa gaa ttc aag agc     336
Leu Pro Ile Gln His Gln Asp Trp Met Ser Gly Lys Glu Phe Lys Ser
            100                 105                 110 aaa gtg aac aac cgg gcc ctg ccc agc ccc atc gag aaa acc atc agc     384
Lys Val Asn Asn Arg Ala Leu Pro Ser Pro Ile Glu Lys Thr Ile Ser
        115                 120                 125 aag ccc aga ggc cct gtg cgg gct cct cag gtg tac gtg ctg ccc cca     432
Lys Pro Arg Gly Pro Val Arg Ala Pro Gln Val Tyr Val Leu Pro Pro
    130                 135                 140 ccc gcc gag gaa atg acc aag aaa gag ttc agc ctg acc agc atg atc     480
Pro Ala Glu Glu Met Thr Lys Lys Glu Phe Ser Leu Thr Ser Met Ile
145                 150                 155                 160 acc ggc ttt ctg ccc gcc gag atc gcc gtg gac tgg acc agc aac ggc     528
Thr Gly Phe Leu Pro Ala Glu Ile Ala Val Asp Trp Thr Ser Asn Gly
                165                 170                 175 cgg acc gag cag aac tac aag aac acc gcc acc gtg ctg gac agc gac     576
Arg Thr Glu Gln Asn Tyr Lys Asn Thr Ala Thr Val Leu Asp Ser Asp
            180                 185                 190 ggc agc tac ttc atg tac agc aag ctg cgg gtg cag aag tcc acc tgg     624
Gly Ser Tyr Phe Met Tyr Ser Lys Leu Arg Val Gln Lys Ser Thr Trp
        195                 200                 205 gag aga ggc agc ctg ttc gcc agc agc gtg gtg cac gag ggc ctg cac     672
Glu Arg Gly Ser Leu Phe Ala Ser Ser Val Val His Glu Gly Leu His
    210                 215                 220 aac cac ctg acc acc aag acc atc agc cgg tcc ctg gga                 711
Asn His Leu Thr Thr Lys Thr Ile Ser Arg Ser Leu Gly
225                 230                 235

<210> SEQ ID NO 28
<211> LENGTH: 237
<212> TYPE: PRT
<213> ORGANISM: Mus musculus

<400> SEQUENCE: 28

Glu Pro Arg Val Pro Ile Thr Gln Asn Pro Ser Pro Pro Leu Lys Glu
1               5                   10                  15

Ser Pro Pro Ser Ala Ala Pro Asp Leu Leu Gly Gly Pro Ser Val Phe
            20                  25                  30

Ile Phe Pro Pro Lys Ile Lys Asp Val Leu Met Ile Ser Leu Ser Pro
```

```
            35                  40                  45
Met Val Thr Ser Val Val Asp Val Ser Glu Asp Pro Asp Val
    50                  55                  60
Gln Ile Ser Trp Phe Val Asn Asn Val Glu Val His Thr Ala Gln Thr
 65                  70                  75                  80
Gln Thr His Arg Glu Asp Tyr Asn Ser Thr Leu Arg Val Val Ser Ala
                85                  90                  95
Leu Pro Ile Gln His Gln Asp Trp Met Ser Gly Lys Glu Phe Lys Ser
            100                 105                 110
Lys Val Asn Asn Arg Ala Leu Pro Ser Pro Ile Glu Lys Thr Ile Ser
        115                 120                 125
Lys Pro Arg Gly Pro Val Arg Ala Pro Gln Val Tyr Val Leu Pro Pro
130                 135                 140
Pro Ala Glu Glu Met Thr Lys Lys Glu Phe Ser Leu Thr Ser Met Ile
145                 150                 155                 160
Thr Gly Phe Leu Pro Ala Glu Ile Ala Val Asp Trp Thr Ser Asn Gly
                165                 170                 175
Arg Thr Glu Gln Asn Tyr Lys Asn Thr Ala Thr Val Leu Asp Ser Asp
            180                 185                 190
Gly Ser Tyr Phe Met Tyr Ser Lys Leu Arg Val Gln Lys Ser Thr Trp
        195                 200                 205
Glu Arg Gly Ser Leu Phe Ala Ser Ser Val Val His Glu Gly Leu His
    210                 215                 220
Asn His Leu Thr Thr Lys Thr Ile Ser Arg Ser Leu Gly
225                 230                 235

<210> SEQ ID NO 29
<211> LENGTH: 15
<212> TYPE: DNA
<213> ORGANISM: Artificial
<220> FEATURE:
<223> OTHER INFORMATION: Synthetic DNA

<400> SEQUENCE: 29
ggtggcggtg gctcg                                                      15

<210> SEQ ID NO 30
<211> LENGTH: 1740
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(1740)

<400> SEQUENCE: 30 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
  1               5                  10                  15 ggt tcc act ggt gac gcg gcc ctc gag gat gca gaa ttc cga cat gac      96
Gly Ser Thr Gly Asp Ala Ala Leu Glu Asp Ala Glu Phe Arg His Asp
             20                  25                  30 tca gga tat gaa gtt cat cat caa aaa ttg gtg ttc ttt gca gaa gat     144
Ser Gly Tyr Glu Val His His Gln Lys Leu Val Phe Phe Ala Glu Asp
         35                  40                  45 gtg ggt tca aac aaa ggt gca atc att gga ctc atg gtg ggc ggt gtt     192
Val Gly Ser Asn Lys Gly Ala Ile Ile Gly Leu Met Val Gly Gly Val
     50                  55                  60
```

```
gtc ata gcg ggt ggc ggt ggc tcg gat gca gaa ttc cga cat gac tca      240
Val Ile Ala Gly Gly Gly Gly Ser Asp Ala Glu Phe Arg His Asp Ser
65              70                  75                  80 gga tat gaa gtt cat cat caa aaa ttg gtg ttc ttt gca gaa gat gtg      288
Gly Tyr Glu Val His His Gln Lys Leu Val Phe Phe Ala Glu Asp Val
                85                  90                  95 ggt tca aac aaa ggt gca atc att gga ctc atg gtg ggc ggt gtt gtc      336
Gly Ser Asn Lys Gly Ala Ile Ile Gly Leu Met Val Gly Gly Val Val
            100                 105                 110 ata gcg ggt ggc ggt ggc tcg gat gca gaa ttc cga cat gac tca gga      384
Ile Ala Gly Gly Gly Gly Ser Asp Ala Glu Phe Arg His Asp Ser Gly
        115                 120                 125 tat gaa gtt cat cat caa aaa ttg gtg ttc ttt gca gaa gat gtg ggt      432
Tyr Glu Val His His Gln Lys Leu Val Phe Phe Ala Glu Asp Val Gly
    130                 135                 140 tca aac aaa ggt gca atc att gga ctc atg gtg ggc ggt gtt gtc ata      480
Ser Asn Lys Gly Ala Ile Ile Gly Leu Met Val Gly Gly Val Val Ile
145                 150                 155                 160 gcg ggt ggc ggt ggc tcg gat gca gaa ttc cga cat gac tca gga tat      528
Ala Gly Gly Gly Gly Ser Asp Ala Glu Phe Arg His Asp Ser Gly Tyr
                165                 170                 175 gaa gtt cat cat caa aaa ttg gtg ttc ttt gca gaa gat gtg ggt tca      576
Glu Val His His Gln Lys Leu Val Phe Phe Ala Glu Asp Val Gly Ser
            180                 185                 190 aac aaa ggt gca atc att gga ctc atg gtg ggc ggt gtt gtc ata gcg      624
Asn Lys Gly Ala Ile Ile Gly Leu Met Val Gly Gly Val Val Ile Ala
        195                 200                 205 ggt acc gag ccc aaa tct tct gac aaa act cac aca tcc cca ccg tcc      672
Gly Thr Glu Pro Lys Ser Ser Asp Lys Thr His Thr Ser Pro Pro Ser
    210                 215                 220 cca gca cct gaa ctc ctg ggg gga ccg tca gtc ttc ctc ttc ccc cca      720
Pro Ala Pro Glu Leu Leu Gly Gly Pro Ser Val Phe Leu Phe Pro Pro
225                 230                 235                 240 aaa ccc aag gac acc ctc atg atc tcc cgg acc cct gag gtc aca tgc      768
Lys Pro Lys Asp Thr Leu Met Ile Ser Arg Thr Pro Glu Val Thr Cys
                245                 250                 255 gtg gtg gtg gac gtg agc cac gaa gac cct gag gtc aag ttc aac tgg      816
Val Val Val Asp Val Ser His Glu Asp Pro Glu Val Lys Phe Asn Trp
            260                 265                 270 tac gtg gac ggc gtg gag gtg cat aat gcc aag aca aag ccg cgg gag      864
Tyr Val Asp Gly Val Glu Val His Asn Ala Lys Thr Lys Pro Arg Glu
        275                 280                 285 gag cag tac aac agc acg tac cgt gtg gtc agc gtc ctc acc gtc ctg      912
Glu Gln Tyr Asn Ser Thr Tyr Arg Val Val Ser Val Leu Thr Val Leu
    290                 295                 300 cac cag gac tgg ctg aat ggc aag gag tac aag tgc aag gtc tcc aac      960
His Gln Asp Trp Leu Asn Gly Lys Glu Tyr Lys Cys Lys Val Ser Asn
305                 310                 315                 320 aaa gcc ctc cca gcc ccc atc gag aaa acc atc tcc aaa gcc aaa ggg     1008
Lys Ala Leu Pro Ala Pro Ile Glu Lys Thr Ile Ser Lys Ala Lys Gly
                325                 330                 335 cag ccc cga gaa cca cag gtg tac acc ctg ccc cca tcc cgg gat gag     1056
Gln Pro Arg Glu Pro Gln Val Tyr Thr Leu Pro Pro Ser Arg Asp Glu
            340                 345                 350 ctg acc aag aac cag gtc agc ctg acc tgc ctg gtc aaa ggc ttc tat     1104
Leu Thr Lys Asn Gln Val Ser Leu Thr Cys Leu Val Lys Gly Phe Tyr
        355                 360                 365 ccc agc gac atc gcc gtg gag tgg gag agc aat ggg cag ccg gag aac     1152
Pro Ser Asp Ile Ala Val Glu Trp Glu Ser Asn Gly Gln Pro Glu Asn
    370                 375                 380
```

```
aac tac aag acc acg cct ccc gtg ctg gac tcc gac ggc tcc ttc ttc    1200
Asn Tyr Lys Thr Thr Pro Pro Val Leu Asp Ser Asp Gly Ser Phe Phe
385                 390                 395                 400 ctc tac agc aag ctc acc gtg gac aag agc agg tgg cag cag ggg aac    1248
Leu Tyr Ser Lys Leu Thr Val Asp Lys Ser Arg Trp Gln Gln Gly Asn
            405                 410                 415 gtc ttc tca tgc tcc gtg atg cat gag gct ctg cac aac cac tac acg    1296
Val Phe Ser Cys Ser Val Met His Glu Ala Leu His Asn His Tyr Thr
                420                 425                 430 cag aag agc ctc tcc ctg tct ccg ggt aaa gtc gac cgc gag aac gcc    1344
Gln Lys Ser Leu Ser Leu Ser Pro Gly Lys Val Asp Arg Glu Asn Ala
        435                 440                 445 aaa gcc aag aca gac cac ggg gcg gag atc gtg tac aag tcg cca gtg    1392
Lys Ala Lys Thr Asp His Gly Ala Glu Ile Val Tyr Lys Ser Pro Val
450                 455                 460 gtg tct ggg gac acg tct cca cgg cat ctc ggt ggc ggt ggc tcg cgc    1440
Val Ser Gly Asp Thr Ser Pro Arg His Leu Gly Gly Gly Gly Ser Arg
465                 470                 475                 480 gag aac gcc aaa gcc aag aca gac cac ggg gcg gag atc gtg tac aag    1488
Glu Asn Ala Lys Ala Lys Thr Asp His Gly Ala Glu Ile Val Tyr Lys
            485                 490                 495 tcg cca gtg gtg tct ggg gac acg tct cca cgg cat ctc ggt ggc ggt    1536
Ser Pro Val Val Ser Gly Asp Thr Ser Pro Arg His Leu Gly Gly Gly
                500                 505                 510 ggc tcg cgc gag aac gcc aaa gcc aag aca gac cac ggg gcg gag atc    1584
Gly Ser Arg Glu Asn Ala Lys Ala Lys Thr Asp His Gly Ala Glu Ile
        515                 520                 525 gtg tac aag tcg cca gtg gtg tct ggg gac acg tct cca cgg cat ctc    1632
Val Tyr Lys Ser Pro Val Val Ser Gly Asp Thr Ser Pro Arg His Leu
530                 535                 540 ggt ggc ggt ggc tcg cgc gag aac gcc aaa gcc aag aca gac cac ggg    1680
Gly Gly Gly Gly Ser Arg Glu Asn Ala Lys Ala Lys Thr Asp His Gly
545                 550                 555                 560 gcg gag atc gtg tac aag tcg cca gtg gtg tct ggg gac acg tct cca    1728
Ala Glu Ile Val Tyr Lys Ser Pro Val Val Ser Gly Asp Thr Ser Pro
            565                 570                 575 cgg cat ctc tga                                                    1740
Arg His Leu <210> SEQ ID NO 31
<211> LENGTH: 579
<212> TYPE: PRT
<213> ORGANISM: Artificial
<220> FEATURE:
<223> OTHER INFORMATION: Synthetic Construct

<400> SEQUENCE: 31

Met Glu Thr Asp Thr Leu Leu Leu Trp Val Leu Leu Leu Trp Val Pro
1               5                   10                  15

Gly Ser Thr Gly Asp Ala Ala Leu Glu Asp Ala Glu Phe Arg His Asp
            20                  25                  30

Ser Gly Tyr Glu Val His His Gln Lys Leu Val Phe Phe Ala Glu Asp
        35                  40                  45

Val Gly Ser Asn Lys Gly Ala Ile Ile Gly Leu Met Val Gly Gly Val
    50                  55                  60

Val Ile Ala Gly Gly Gly Ser Asp Ala Glu Phe Arg His Asp Ser
65                  70                  75                  80

Gly Tyr Glu Val His His Gln Lys Leu Val Phe Phe Ala Glu Asp Val
                85                  90                  95
```

```
Gly Ser Asn Lys Gly Ala Ile Ile Gly Leu Met Val Gly Val Val
            100                 105                 110
Ile Ala Gly Gly Gly Ser Asp Ala Glu Phe Arg His Asp Ser Gly
            115                 120                 125
Tyr Glu Val His His Gln Lys Leu Val Phe Phe Ala Glu Asp Val Gly
            130                 135                 140
Ser Asn Lys Gly Ala Ile Ile Gly Leu Met Val Gly Gly Val Val Ile
145                 150                 155                 160
Ala Gly Gly Gly Ser Asp Ala Glu Phe Arg His Asp Ser Gly Tyr
                165                 170                 175
Glu Val His His Gln Lys Leu Val Phe Phe Ala Glu Asp Val Gly Ser
                180                 185                 190
Asn Lys Gly Ala Ile Ile Gly Leu Met Val Gly Gly Val Val Ile Ala
            195                 200                 205
Gly Thr Glu Pro Lys Ser Ser Asp Lys Thr His Thr Ser Pro Pro Ser
            210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
            275                 280                 285
Glu Gln Tyr Asn Ser Thr Tyr Arg Val Val Ser Val Leu Thr Val Leu
            290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Asp Glu
            340                 345                 350
Leu Thr Lys Asn Gln Val Ser Leu Thr Cys Leu Val Lys Gly Phe Tyr
            355                 360                 365
Pro Ser Asp Ile Ala Val Glu Trp Glu Ser Asn Gly Gln Pro Glu Asn
            370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
                420                 425                 430
Gln Lys Ser Leu Ser Leu Ser Pro Gly Lys Val Asp Arg Glu Asn Ala
            435                 440                 445
Lys Ala Lys Thr Asp His Gly Ala Glu Ile Val Tyr Lys Ser Pro Val
            450                 455                 460
Val Ser Gly Asp Thr Ser Pro Arg His Leu Gly Gly Gly Ser Arg
465                 470                 475                 480
Glu Asn Ala Lys Ala Lys Thr Asp His Gly Ala Glu Ile Val Tyr Lys
                485                 490                 495
Ser Pro Val Val Ser Gly Asp Thr Ser Pro Arg His Leu Gly Gly Gly
            500                 505                 510
```

```
Gly Ser Arg Glu Asn Ala Lys Ala Lys Thr Asp His Gly Ala Glu Ile
        515                 520                 525

Val Tyr Lys Ser Pro Val Val Ser Gly Asp Thr Ser Pro Arg His Leu
    530                 535                 540

Gly Gly Gly Gly Ser Arg Glu Asn Ala Lys Ala Lys Thr Asp His Gly
545                 550                 555                 560

Ala Glu Ile Val Tyr Lys Ser Pro Val Val Ser Gly Asp Thr Ser Pro
                565                 570                 575

Arg His Leu

<210> SEQ ID NO 32
<211> LENGTH: 69
<212> TYPE: DNA
<213> ORGANISM: Homo sapiens
<220> FEATURE:
<221> NAME/KEY: CDS
<222> LOCATION: (1)..(69)

<400> SEQUENCE: 32 atg gag aca gac aca ctc ctg cta tgg gta ctg ctg ctc tgg gtt cca      48
Met Glu Thr Asp Thr Leu Leu Leu Trp Val Leu Leu Leu Trp Val Pro
1               5                   10                  15 ggt tcc act ggt gac gcg gcc                                          69
Gly Ser Thr Gly Asp Ala Ala
            20

<210> SEQ ID NO 33
<211> LENGTH: 23
<212> TYPE: PRT
<213> ORGANISM: Homo sapiens

<400> SEQUENCE: 33

Met Glu Thr Asp Thr Leu Leu Leu Trp Val Leu Leu Leu Trp Val Pro
1               5                   10                  15

Gly Ser Thr Gly Asp Ala Ala
            20

<210> SEQ ID NO 34
<211> LENGTH: 549
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(549)

<400> SEQUENCE: 34 gat gca gaa ttc cga cat gac tca gga tat gaa gtt cat cat caa aaa      48
Asp Ala Glu Phe Arg His Asp Ser Gly Tyr Glu Val His His Gln Lys
1               5                   10                  15 ttg gtg ttc ttt gca gaa gat gtg ggt tca aac aaa ggt gca atc att      96
Leu Val Phe Phe Ala Glu Asp Val Gly Ser Asn Lys Gly Ala Ile Ile
            20                  25                  30 gga ctc atg gtg ggc ggt gtt gtc ata gcg ggt ggc ggt ggc tcg gat     144
Gly Leu Met Val Gly Gly Val Val Ile Ala Gly Gly Gly Gly Ser Asp
        35                  40                  45 gca gaa ttc cga cat gac tca gga tat gaa gtt cat cat caa aaa ttg     192
Ala Glu Phe Arg His Asp Ser Gly Tyr Glu Val His His Gln Lys Leu
    50                  55                  60 gtg ttc ttt gca gaa gat gtg ggt tca aac aaa ggt gca atc att gga     240
Val Phe Phe Ala Glu Asp Val Gly Ser Asn Lys Gly Ala Ile Ile Gly
65                  70                  75                  80
```

```
ctc atg gtg ggc ggt gtt gtc ata gcg ggt ggc ggt ggc tcg gat gca      288
Leu Met Val Gly Gly Val Val Ile Ala Gly Gly Gly Gly Ser Asp Ala
            85                  90                  95 gaa ttc cga cat gac tca gga tat gaa gtt cat cat caa aaa ttg gtg      336
Glu Phe Arg His Asp Ser Gly Tyr Glu Val His His Gln Lys Leu Val
                100                 105                 110 ttc ttt gca gaa gat gtg ggt tca aac aaa ggt gca atc att gga ctc      384
Phe Phe Ala Glu Asp Val Gly Ser Asn Lys Gly Ala Ile Ile Gly Leu
            115                 120                 125 atg gtg ggc ggt gtt gtc ata gcg ggt ggc ggt ggc tcg gat gca gaa      432
Met Val Gly Gly Val Val Ile Ala Gly Gly Gly Gly Ser Asp Ala Glu
        130                 135                 140 ttc cga cat gac tca gga tat gaa gtt cat cat caa aaa ttg gtg ttc      480
Phe Arg His Asp Ser Gly Tyr Glu Val His His Gln Lys Leu Val Phe
145                 150                 155                 160 ttt gca gaa gat gtg ggt tca aac aaa ggt gca atc att gga ctc atg      528
Phe Ala Glu Asp Val Gly Ser Asn Lys Gly Ala Ile Ile Gly Leu Met
                165                 170                 175 gtg ggc ggt gtt gtc ata gcg                                          549
Val Gly Gly Val Val Ile Ala
            180

<210> SEQ ID NO 35
<211> LENGTH: 183
<212> TYPE: PRT
<213> ORGANISM: Artificial
<220> FEATURE:
<223> OTHER INFORMATION: Synthetic Construct

<400> SEQUENCE: 35

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Gly Gly Gly Gly Ser Asp
            35                  40                  45

Ala Glu Phe Arg His Asp Ser Gly Tyr Glu Val His His Gln Lys Leu
        50                  55                  60

Val Phe Phe Ala Glu Asp Val Gly Ser Asn Lys Gly Ala Ile Ile Gly
65                  70                  75                  80

Leu Met Val Gly Gly Val Val Ile Ala Gly Gly Gly Gly Ser Asp Ala
                85                  90                  95

Glu Phe Arg His Asp Ser Gly Tyr Glu Val His His Gln Lys Leu Val
            100                 105                 110

Phe Phe Ala Glu Asp Val Gly Ser Asn Lys Gly Ala Ile Ile Gly Leu
        115                 120                 125

Met Val Gly Gly Val Val Ile Ala Gly Gly Gly Gly Ser Asp Ala Glu
    130                 135                 140

Phe Arg His Asp Ser Gly Tyr Glu Val His His Gln Lys Leu Val Phe
145                 150                 155                 160

Phe Ala Glu Asp Val Gly Ser Asn Lys Gly Ala Ile Ile Gly Leu Met
                165                 170                 175

Val Gly Gly Val Val Ile Ala
            180
```